United States Patent
Nawarathna et al.

(10) Patent No.: US 10,794,894 B2
(45) Date of Patent: Oct. 6, 2020

(54) INTEGRATED DIELECTROPHORETIC AND SURFACE PLASMONIC APPARATUS AND METHODS FOR IMPROVEMENT IN THE DETECTION OF BIOLOGICAL MOLECULES

(71) Applicant: NDSU Research Foundation, Fargo, ND (US)

(72) Inventors: Dharmakeerthi Nawarathna, Fargo, ND (US); Logeeshan Velmanickam, Fargo, ND (US)

(73) Assignee: NDSU Research Foundation, Fargo, ND (US)

(*) Notice: Subject to any disclaimer, the term of this patent is extended or adjusted under 35 U.S.C. 154(b) by 3 days.

(21) Appl. No.: 16/108,957

(22) Filed: Aug. 22, 2018

(65) Prior Publication Data
US 2019/0064139 A1  Feb. 28, 2019

Related U.S. Application Data

(60) Provisional application No. 62/548,764, filed on Aug. 22, 2017.

(51) Int. Cl.
*G01N 33/487* (2006.01)
*C12Q 1/6825* (2018.01)
*B03C 5/02* (2006.01)
*G01N 27/447* (2006.01)
*B03C 5/00* (2006.01)

(52) U.S. Cl.
CPC .......... *G01N 33/487* (2013.01); *B03C 5/005* (2013.01); *B03C 5/026* (2013.01); *C12Q 1/6825* (2013.01); *G01N 27/447* (2013.01); *B01L 2400/0424* (2013.01); *B03C 2201/26* (2013.01)

(58) Field of Classification Search
CPC .............................. G01N 33/487; B03C 5/005
See application file for complete search history.

(56) References Cited

U.S. PATENT DOCUMENTS 6,645,359 B1* 11/2003 Bhullar .................. C12Q 1/001
204/403.01
2005/0112544 A1* 5/2005 Xu ........................ C12M 23/12
435/4

OTHER PUBLICATIONS

Osman, I., Bajorin, D.F., Sun, T.T., Zhong, H., Douglas, D., Scattergood, J., Zheng, R., Han, M., Marshall, K.W. and Liew, C.C., 2006. Novel blood biomarkers of human urinary bladder cancer. Clinical Cancer Research, 12(11), pp. 3374-3380.
Patterson, G.H., Knobel, S.M., Sharif, W.D., Kain, S.R. and Piston, D.W. Use of the green fluorescent protein and its mutants in quantitative fluorescence microscopy. Biophysical journal. 1997, 73(5), 2782.
Pethig, R. Review article—dielectrophoresis: status of the theory, technology, and applications. Biomicrofluidics, 2010, 4(2), p. 022811.
Pethig, R., and Markx, G. H. (1997). Applications of dielectrophoresis in biotechnology. Trends in biotechnology, 15(10), 426-432.
Pommer, M.S., Zhang, Y., Keerthi, N., Chen, D., Thomson, J.A., Meinhart, C.D. and Soh, H.T. Dielectrophoretic separation of platelets from diluted whole blood in microfluidic channels. Electrophoresis. 2008, 29 (6), 1213-1218.
Roy, S., Soh, J.H. and Gao, Z., 2011. A microfluidic-assisted microarray for ultrasensitive detection of miRNA under an optical microscope. Lab on a Chip, 11(11), pp. 1886-1894.
Rusling, James F., et al. Measurement of biomarker proteins for point-of-care early detection and monitoring of cancer. Analyst. 2010, 135(10), 2496-2511.
Sanghavi, B.J., Varhue, W., Rohani, A., Liao, K.T., Bazydlo, L.A., Chou, C.F. and Swami, N.S., Ultrafast immunoassays by coupling dielectrophoretic biomarker enrichment in nanoslit channel with electrochemical detection on graphene. Lab on a Chip, 2015, 15(24), 4563-4570.
Sharma, H., Digman, M. A., Felsinger, N., Gratton, E., and Khine, M. Enhanced emission of fluorophores on shrink-induced wrinkled composite structures. Optical materials express. 2014, 4(4), 753-763.
Steinberg, W. (1990). The clinical utility of the CA 19-9 tumor-associated antigen. American Journal of Gastroenterology, 85(4).
Tricoli, J.V. and Jacobson, J.W., 2007. MicroRNA: potential for cancer detection, diagnosis, and prognosis. Cancer research, 67(10), pp. 4553-4555.
Wang, X.B., Yang, J., Huang, Y., Vykoukal, J., Becker, F.F. and Gascoyne, P.R., 2000. Cell separation by dielectrophoretic field-flow-fractionation. Analytical Chemistry, 72(4), pp. 832-839.
Wen, Y., Pei, H., Shen, Y., Xi, J., Lin, M., Lu, N., Shen, X., Li, J. and Fan, C., 2012. DNA nanostructure-based interfacial engineering for PCR-free ultrasensitive electrochemical analysis of microRNA. Scientific reports, 2, p. 867.
White I.M., Yazdi, S.H. and Wei, W.Y. Optofluidic SERS: synergizing photonics and microfluidics for chemical and biological analysis. Microfluidics and nanofluidics. 2012, 13(2), 205-216.
Wolcott, M.J., Advances in nucleic acid-based detection methods. Clinical microbiology reviews, 1992, 5(4), 370-386.
Zheng, L., Brody, J.P. and Burke, P.J., Electronic manipulation of DNA, proteins, and nanoparticles for potential circuit assembly. Biosensors and Bioelectronics, 2004, 20(3), 606-619.
Zou, Z., Kai, J., Rust, M. J., Han, J., and Ahn, C. H. Functionalized nano interdigitated electrodes arrays on polymer with integrated microfluidics for direct bio-affinity sensing using impedimetric measurement. Sensors and Actuators A: Physical. 2007, 136(2), 518-526.
Altissimo, M., 2010. E-beam lithography for micro-/nanofabrication. Biomicrofluidics, 4(2), p. 026503.

(Continued)

*Primary Examiner* — Narayan K Bhat
(74) *Attorney, Agent, or Firm* — Stites & Harbison, PLLC; Mandy Wilson Decker; Summer E. Young

(57) ABSTRACT

The present invention relates to an apparatus and methods for an integrated dielectrophoretic (DEP) and surface plasmonic platform to quantify as little as 1 femptomolar to 1 picomolar of fluorescent molecules in low conductivity buffers.

4 Claims, 13 Drawing Sheets

(56) References Cited

OTHER PUBLICATIONS

Anderson, Leigh. "Candidate-based proteomics in the search for biomarkers of cardiovascular disease." The Journal of physiology 563.1 (2005): 23-60.

Anderson, N. Leigh, and Norman G. Anderson. "The human plasma proteome history, character, and diagnostic prospects." Molecular & cellular proteomics 1.11 (2002): 845-867.

Bettazzi, Francesca, et al. "Electrochemical detection of miRNA-222 by use of a magnetic bead-based bioassay." Analytical and bioanalytical chemistry 405.2-3 (2013): 1025-1034.

Chen, Caifu, et al. "Real-time quantification of microRNAs by stem-loop RT-PCR" Nucleic acids research 33.20 (2005): e179-e179.

Cissell, Kyle A., and Sapna K. Deo. "Trends in microRNA detection." Analytical and bioanalytical chemistry 394.4 (2009): 1109-1116.

Duhr, S. and Braun, D., 2006. Optothermal molecule trapping by opposing fluid flow with thermophoretic drift. Physical review letters, 97(3), p. 038103.

Eguia, Vasco, Tamas Adam Gonda, and Muhammad Wasif Saif. "Early detection of pancreatic cancer." JOP. Journal of the Pancreas 13.2 (2012): 131-134.

Ezzati, Majid, et al. "Selected major risk factors and global and regional burden of disease." The Lancet 360.9343 (2002): 1347-1360.

Friedländer, Marc R., et al. "Discovering microRNAs from deep sequencing data using miRDeep." Nature biotechnology 26.4 (2008).

Habbe, Nils, et al. "MicroRNA miR-155 is a biomarker of early pancreatic neoplasia." Cancer biology & therapy 8.4 (2009): 340-346.

Hingorani, Sunil R., et al. "Preinvasive and invasive ductal pancreatic cancer and its early detection in the mouse." Cancer cell 4.6 (2003): 437-450.

Huang, Zhaohui, et al. "Plasma microRNAs are promising novel biomarkers for early detection of colorectal cancer" International journal of cancer 127.1 (2010): 118-126.

Lodes, Michael J., et al. "Detection of cancer with serum miRNAs on an oligonucleotide microarray." PloS one 4.7 (2009): e6229.

Lopez Alan D., et al. "Global and regional burden of disease and risk factors, 2001: systematic analysis of population health data." The Lancet 367.9524 (2006): 1747-1757.

Lusi, E. A., et al."Innovative electrochemical approach for an early detection of microRNAs." Analytical chemistry 813 (2009): 2819-2822.

Marafona, J. and Chousal, J.A.G., 2006. A finite element model of EDM based on the Joule effect. International Journal of Machine Tools and Manufacture, 46(6), pp. 595-602.

Murray, Christopher J.L., et al. "The global burden of disease: a comprehensive assessment of mortality and disability from diseases, injuries, and risk factors in 1990 and projected to 2020: summary." (1996).

Reichl, M., Herzog, M., Greiss, F., Wolff, M. and Braun, D., 2015. Understanding the similarity in thermophoresis between single-and double-stranded DNA or RNA. Physical Review E, 91(6), p. 062709.

Varkonyi-Gasic, Erika, et al. "Protocol: a highly sensitive RT-PCR method for detection and quantification of microRNAs." Plant methods 3.1 (2007): 12.

Velmanickam, Logeeshan, et al. "Integrated dielectrophoretic and surface plasmonic platform for million-fold improvement in the detection of fluorescent events." Biomicrofluidics 11.4 (2017): 044115.

Vomhof-Dekrey, E.E., Hermann, R.J., Palmer, M.F., Benton, K.D., Sandy, A.R., Dorsam, S.T. and Dorsam, G.P., 2008. TCR signaling and environment affect vasoactive intestinal peptide receptor-1 (VPAC-1) expression in primary mouse CD4 T cells. Brain, behavior, and immunity, 22(7), pp. 1032-1040.

Wei, Juan, et al. "Identification of plasma microRNA-21 as a biomarker for early detection and chemosensitivity of non-small cell lung cancer." Chinese journal of cancer 30.6 (2011): 407.

Yin, Huanshun, et al. "An electrochemical signal 'off-on'sensing platform for microRNA detection." Analyst 137.6 (2012): 1389-1395.

Asbury, C.L., Diercks, A.H. and Van Den Engh, G., 2002. Trapping of DNA by dielectrophoresis. Electrophoresis, 23(16), pp. 2658-2666.

Barik, Avijit, et al. Dielectrophoresis-enhanced plasmonic sensing with gold nanohole arrays. Nano letters. 2014, 14 (4), 2006-2012.

Basuray, S. and Chang, H.C.,. Induced dipoles and dielectrophoresis of nanocolloids in electrolytes. Physical Review E, 2007,75(6), 060501.

Beger, H. G., Rau, B., Gansauge, F., Poch, B., and Link, K. H. (2003). Treatment of pancreatic cancer: challenge of the facts. World journal of surgery, 27(10), 1075-1084.

Brismar, H., Trepte, O. and Ulfhake, B. Spectra and fluorescence lifetimes of lissamine rhodamine, tetramethylrhodamine isothiocyanate, texas red, and cyanine 3.18 fluorophores: influences of some environmental factors recorded with a confocal laser scanning microscope. Journal of Histochemistry & Cytochemistry. 1995, 43(7), 699-707.

Čemažar, J., Douglas, T.A., Schmelz, E.M. and Davalos, R.V. Enhanced contactless dielectrophoresis enrichment and isolation platform via cell-scale microstructures. Biomicrofluidics, 2016 10(1), 014109.

Chaurey, V., Rohani, A., Su, Y.H., Liao, K.T., Chou, C.F. and Swami, N.S., Scaling down constriction-based (electrodeless) dielectrophoresis devices for trapping nanoscale bioparticles in physiological media of high-conductivity. Electrophoresis, 2013, 34(7), pp. 1097-1104.

Chen, X., Ba, Y., Ma, L., Cai, X., Yin, Y., Wang, K., Guo, J., Zhang, Y., Chen, J., Guo, X. and Li, Q., 2008. Characterization of microRNAs in serum: a novel class of biomarkers for diagnosis of cancer and other diseases. Cell research, 18(10), pp. 997-1006.

Cheng, I.F., Senapati, S., Cheng, X., Basuray, S., Chang, H.C. and Chang, H.C., A rapid field-use assay for mismatch number and location of hybridized DNAs. Lab on a Chip, 2010, 10(7), pp. 828-831.

Chou, C.F., Tegenfeldt, J.O., Bakajin, O., Chan, S.S., Cox, E.C., Darnton, N., Duke, T. and Austin, R.H., 2002. Electrodeless dielectrophoresis of single-and double-stranded DNA. Biophysical Journal, 83(4), pp. 2170-2179.

Clarke, R.W., White, S.S., Zhou, D., Ying, L. and Klenerman, D., Trapping of proteins under physiological conditions in a nanopipette. Angewandte Chemie International Edition, 2005, 44(24), 3747-3750.

Cuervo, A., Dans, P.D., Carrascosa, J.L., Orozco, M., Gomila, G. and Fumagalli, L. Direct measuremeni of the dielectric polarization properties of DNA. Proceedings of the National Academy of Sciences, 2014, 111(35), E3624-E3630.

Dutta Choudhury, S., Badugu, R., Ray, K. and Lakowicz, J.R. Silver-gold nanocomposite substrates for metal-enhanced fluorescence: Ensemble and single-molecule spectroscopic studies. The Journal of Physical Chemistry C. 2012, 116(8), 5042-5048.

Ermolina, I. and Morgan, H., The electrokinetic properties of latex particles: comparison of electrophoresis and dielectrophoresis. Journal of colloid and interface science, 2005, 285(1), pp. 419-428.

Frebourg, T., Bercoff, E., Manchon, N., Senant, J., Basuyau, J. P., Breton, P., and Boureille, J. (1988). The evaluation of CA 19-9 antigen level in the early detection of pancreatic cancer. Cancer, 62(11), 2287-2550.

Fu, C.C., Ossato, G., Long, M., Digman, M.A., Gopinathan, A., Lee, L.P., Gratton, E. and Khine, M. Bimetallic nanopetals for thousand-fold fluorescence enhancements. Applied Physics Letters. 2010, 97(20), 203101.

Ganepola, G.A., Rutledge, J.R., Suman, P., Yiengpruksawan, A. and Chang, D.H., 2014. Novel blood-based microRNA biomarker panel for early diagnosis of pancreatic cancer. World J Gastrointest Oncol, 6(1), pp. 22-33.

Gascoyne, P.R. and Vykoukal, J., 2002. Particle separation by dielectrophoresis. Electrophoresis, 23(13), p. 1973.

Geddes, C.D. and Lakowicz, J.R. Editorial: metal-enhanced fluorescence. Journal of Fluorescence. 12(2), 2002, 12, 121-129.

(56) References Cited

OTHER PUBLICATIONS

Goonetilleke, K. S., and Siriwardena, A. K. (2007). Systematic review of carbohydrate antigen (CA 19-9) as a biochemical marker in the diagnosis of pancreatic cancer. European Journal of Surgical Oncology (EJSO), 33(3), 266-270.
Gupta, V., Jafferji, I., Garza, M., Melnikova, V.O., Hasegawa, D.K., Pethig, R. and Davis, D.W. ApoStream™, a new dielectrophoretic device for antibody independent isolation and recovery of viable cancer cells from blood. Biomicrofluidics, 2012, 6(2), 024133.
Huang, Y., Joo, S., Duhon, M., Heller, M., Wallace, B. and Xu, X., 2002. Dielectrophoretic cell separation and gene expression profiling on microelectronic chip arrays. Analytical chemistry, 74(14), pp. 3362-3371.
Hughes, M.P., Morgan, H. and Flynn, M.F.,. The dielectrophoretic behavior of submicron latex spheres: Influence of surface conductance. Journal of colloid and interface science, 220(2), 1999, 454-457.
Iandolo, B., Antosiewicz, T. J., Hellman, A., and Zorić, I. On the mechanism for nanoplasmonic enhancement of photon to electron conversion in nanoparticle sensitized hematite films. Physical Chemistry Chemical Physics. 2013, 15(14), 4947-4954.
Jackson, J.D., 1999. Classical electromagnetics. J. Wiley & Sons, Inc., Singapore, pp. 330-335.
Jolley, M.E, Wang, C.H.J., Ekenberg, S.J., Zuelke, M.S. and Kelso, D.M. Particle concentration fluorescence immunoassay (PCFIA): a new, rapid immunoassay technique with high sensitivity. Journal of immunological methods. 1984, 67(1), 21-35.
Kawabata, T. and Washizu, M., 2001 Dielectrophoretic detection of molecular bindings. IEEE Transactions on Industry Applications, 37(6), pp. 1625-1633.
Kim, Dongwoo, Weston L. Daniel, and Chad A. Mirkin. Microarray-based multiplexed scanometric immunoassay for protein cancer markers using gold nanoparticle probes. Analytical chemistry. 2009, 81(21), 9183-9187.
Kim, S.K., Hesketh, P.J., Li, C., Thomas, J.H., Halsall, H.B. and Heineman, W.R. Fabrication of comb interdigitated electrodes array (IDA) for a microbead-based electrochemical assay system. Biosensors and Bioelectronics. 2004, 20(4), 887-894.
Kosaka, N., Iguchi, H. and Ochiya, T., 2010. Circulating microRNA in body fluid: a new potential biomarker for cancer diagnosis and prognosis. Cancer science, 101(10), pp. 2087-2092.
Lakowicz, J.R., 2001. Radiative decay engineering: biophysical and biomedical applications. Analytical biochemistry, 298(1), pp. 1-24.
Lee, E.J., Gusev, Y., Jiang, J., Nuovo, G.J., Lerner, M.R., Frankel, W.L., Morgan, D.L., Postier, R.G., Brackett, D.J. and Schmittgen, T.D., 2007. Expression profiling identifies microRNA signature in pancreatic cancer. International journal of cancer, 120(5), pp. 1046-1054.
Li, H. and Bashir, R. Dielectrophoretic separation and manipulation of live and heat-treated cells of Listeria on microfabricated devices with interdigitated electrodes. Sensors and Actuators B: Chemical. 2002, 86(2), 215-221.
Liao, K.T., Tsegaye, M., Chaurey, V., Chou, C.F. and Swami, N.S., Nano-constriction device for rapid protein preconcentration in physiological media through a balance of electrokinetic forces. Electrophoresis, 2012, 33(13), pp. 1958-1966.

Lisi, P.J., Huang, C.W., Huffman, R.A. and Teipel, J.W. A fluorescence immunoassay for soluble antigens employing flow cytometric detection. Clinica Chimica Acta. 1982, 120(2), 171-179.
Epstein, J.R. and Walt, D.R. Fluorescence-based fibre optic arrays: a universal platform for sensing. Chemical Society Reviews. 2003, 32(4), 203-214.
Liu, R., Chen, X., Du, Y., Yao, W., Shen, L., Wang, C., Hu, Z., Zhuang, R., Ning, G., Zhang, C. and Yuan, Y., 2012. Serum microRNA expression profile as a biomarker in the diagnosis and prognosis of pancreatic cancer. Clinical chemistry, 58(3), pp. 610-618.
Lofton-Day, C., Model, F., Devos, T., Tetzner, R., Distler, J., Schuster, M., Song, X., Lesche, R., Liebenberg, V., Ebert, M. and Molnar, B., 2008. DNA methylation biomarkers for blood-based colorectal cancel screening. Clinical chemistry, 54(2), pp. 414-423.
Lu, Guowei, et al. Plasmonic-enhanced molecular fluorescence within isolated bowtie nano-apertures. Acs Nano. 2012, 6(2) ,1438-1448.
Lu, Y., Liu, T., Lamanda, A.C., Sin, M.L., Gau, V., Liao, J.C. and Wong, P.K., AC electrokinetics of physiological fluids for biomedical applications, Journal of laboratory automation, 2015, 20(6), pp. 611-620.
Maier, Stefan A., and Harry A. Atwater. Plasmonics: Localization and guiding of electromagnetic energy in metal/dielectric structures. Journal of Applied Physics. 2005, 98(1), 011101.
Mendes, P.M., Jacke, S., Critchley, K., Plaza, J., Chen, Y., Nikitin, K., Palmer, R.E., Preece, J.A., Evans, S.D. and Fitzmaurice, D., Gold nanoparticle patterning of silicon wafers using chemical e-beam lithography. Langmuir, 2004, 20(9), 3766-3768.
Mitchell, P.S., Parkin, R.K., Kroh, E.M., Fritz, B.R., Wyman, S.K., Pogosova-Agadjanyan, E.L., Peterson, A., Noteboom, J., O'Briant, K.C., Allen, A. and Lin, D.W., 2008. Circulating microRNAs as stable blood-based markers for cancer detection. Proceedings of the National Academy of Sciences, 105(30), pp. 10513-10518.
Miura, F., Takada, T., Amano, H., Yoshida, M., Furui, S., and Takeshita, K. (2006). Diagnosis of pancreatic cancer. HPB, 8(5), 337-342.
Morgan, H., Hughes, M. P., and Green, N. G. (1999). Separation of submicron bioparticles by dielectrophoresis. Biophysical journal, 77(1), 516-525.
Mulvihill, M. J., Ling, X. Y., Henzie, J., and Yang, P. Anisotropic etching of silver nanoparticles for plasmonic structures capable of single-particle SERS. Journal of the American Chemical Society. 2009, 132(1), 268-274.
Nakano, A. and Ros, A., Protein dielectrophoresis: advances, challenges, and applications. Electrophoresis, 2013, 34(7), 1085-1096.
Nakano, A., Luo, J. and Ros, A., Temporal and spatial temperature measurement in insulator-based dielectrophoretic devices. Analytical chemistry, 2014, 86(13), pp. 6516-6524.
Nawarathna, D., Norouzi, N., McLane, J., Sharma, H., Sharac, N., Grant, T., Chen, A., Strayer, S., Ragan, R. and Khine, M. Shrink-induced sorting using integrated nanoscale magnetic traps. Applied physics letters. 2013, 102(6), 063504.
Nawarathna, D., Turan, T. and Wickramasinghe, H.K. Selective probing of mRNA expression levels within a living cell. Applied physics letters. 2009, 95(8), 083117.

\* cited by examiner

INTEGRATED DIELECTROPHORETIC AND SURFACE PLASMONIC APPARATUS AND METHODS FOR IMPROVEMENT IN THE DETECTION OF BIOLOGICAL MOLECULES

RELATED APPLICATIONS

This application claims the benefit of U.S. Provisional Application Ser. No. 62/548,764, filed Aug. 22, 2017, the entire disclosure of which is incorporated herein by this reference.

TECHNICAL FIELD

The presently-disclosed subject matter generally relates to products and methods for an integrated dielectrophoretic (DEP) and surface plasmonic platform to quantify as little as approximately 1 femtomolar of fluorescent molecules in low conductivity buffers.

BACKGROUND

Quantification of biomarker molecules, such as proteins, DNA molecules, and RNA molecules, in biological samples, such as blood, saliva, and serum, is routinely performed to assess various stages of diseases and to develop therapeutic strategies for disease elimination or control [Jolley 1984, Lisi 1982]. Among the promising methods to quantify these biomarker molecules, fluorescence-based optical sensing techniques involve fluorescently labeling and measuring the fluorescence intensity of the target biomarkers in the sample. The fluorescence intensity is then converted to molarity and the number of target molecules [Epstein 2003]. The detection limit (or limit of detection) is an important factor in sensing because it indicates the smallest amount of detectable molecules. The limit of fluorescence detection is not sufficient to detect many disease-related biomarkers, especially in the early stages of disease development [Patterson 1997]. To address this issue, interactions of metal surfaces, particles and colloids with fluorophore molecules have been utilized in assays. These metallic components increase the electric field (felt by the fluorophore) and subsequently decrease the radiative decay rate of the fluorophore [Lakowicz 2001]. Radiative decay rate is the spontaneous rate at which a fluorophore emits photons [Lakowicz 2001]. These effects cause a significant increase in the quantum yield and decrease in the fluorescence lifetime [Lakowicz 2001]. As a direct result, the fluorescence intensity of the fluorophore significantly increases, and the fluorophore can easily be recognized from the background white noise [Lakowicz 2001]. Therefore, the detection limit of the fluorescence-based assays can be significantly improved. Studies using silver or gold colloidal metal films and placing fluorophore molecules near those metals have reported producing undesirable chemical reactions between the fluorophore and metals such as metal etching by halide ions [Geddes 2002]. Therefore, additional studies were performed with modified metal colloidal films using about 10-nm glass films, and these studies reported an approximate 20-fold enhancement of fluorescence [Geddes 2002].

Additionally, nano-fabricated metallic nano-structures have been used in experiments to further improve the fluorescence enhancement of fluorescence-based assays [Fu 2010, Lakowicz 2001]. Fabrication of metallic nano-structures is typically performed using an E-beam lithography tool [Mendes 2004]. Unfortunately, production of metallic nano-structures using an E-beam lithography tool is a complicated process that is expensive, time-consuming and can produce only small amount of nano-structures that can handle only small sample volumes. Thus, nano-fabricated metallic nanostructures with E-beam lithography is not feasible in a real diagnosis assay. To address this issue, studies have focused on producing metallic nano-structures using non-conventional methods [Fu 2010, Bank 2014]. These nano-structures are easy to manufacture, cost effective and sufficient for handling large sample volumes. With these structures, studies have focused on improving the detection limits and sensitivity of fluorescence-based assays, particularly using the fluorophore and metal interactions, which are also called surface plasmonic effects [Fu 2010, Barik 2014]. In these methods, the interaction of metallic nanostructures and fluorescently labeled biomarkers near metal and dielectric interfaces was utilized to quantify biomarkers as they increase fluorescence intensity [Fu 2010, White 2012, Dutta 2012]. For example, Fu et al. demonstrated an increase of up to 4,000-fold in the fluorescence emission [Fu 2010].

To drastically improve the detection limit of all these plasmonic-based sensing techniques, fluorescently labeled biomarkers would need to be placed within about 100 nm from metallic nanostructures (hotspots) [Fu 2010, Geddes 2002, Lakowicz 2001]. Because of this limitation, detection is limited to the molecules that are about <100 nm from hotspots. To address this issue, dielectrophoretic force (DEP) was used to place the biomarkers on hotspots and studied the fluorescence intensity and lifetime. DEP is a direct result of dielectrophoresis, a process in which biomolecules experience a force, resulting in movement to the area that has the highest or lowest electric field gradient ($\nabla(|E|^2)$) [Nawarathna 2009]. Theoretical studies have shown that metallic nanostructures produce a greater fluorescence enhancement compared with the colloidal metal films, and thus, metallic nanostructures were selected for an embodiment of the present invention [Geddes 2002].

Studies have used DEP to manipulate DNA, mRNA, miRNA and protein molecules [Pommer 2008, Nawarathna 2009, Cheng 2010, Zheng 2004, Nakano 2013, Liao 2012]. Additionally, studies have utilized integrated approaches that combine DEP with other methods to detect biomolecules [Cheng 2010, Sanghavi 2015]. In one embodiment of the present invention, fluorescently labeled Avidin (protein) molecules were used. Detection of protein is specifically important in diagnosis but most protein detection applications currently rely on traditional methods such as spectrometry and antibody-dependent methods. However, there are several sensitive methods available for detection of nucleic acids (DNA, mRNA and miRNA), such as real-time polymerase chain reaction, micro-array techniques and gel electrophoresis [Wolcott 1992]. These methods are commonly used and detection limits down to a few molecules are possible using these methods. In this regard, studies have reported detecting up to fM levels of nucleic acids [Cheng 2010].

Dielectric properties of nucleic acids were investigated by number of research groups and reported that nucleic acids have semiconducting-like properties [Zheng 2004, Clarke 2005]. In addition, frequency dependent polarization mechanisms are well understood for nucleic acid molecules [Cuervo 2014, Pethig 2010]. Therefore, designing and implementation of assays that involve DEP forces are doable. In comparison, studies have reported that dielectric properties of proteins are more diverse than nucleic acids and dependent on a number of parameters such as buffer conditions, molarity and size of the proteins [Zheng 2004]. Therefore, development of sensing assays that use DEP is challenging. Studies that are focused only on using plasmonic effects to detect proteins have reported the detection limit of 1 μM [Kim 2009, Rusling 2010]. Mathematically, DEP force acting on biomarker molecules is represented as $$F_{DEP}=\frac{1}{2}\alpha\nabla(|E|^2), \quad (1)$$

where α is the polarizability of the biomarker, ∇ is the gradient operator, and E is the root-mean square (r.m.s) of the electric field [Nawarathna 2009]. For a spherical particle $$\alpha=4\pi\varepsilon_m r^3 Re\{f_{CM}(\omega)\}, \quad (2)$$

where r is the radius of the particle, $\varepsilon_m$ is the suspending medium permittivity, ω is the frequency of the applied electric field, and $Re\{f_{CM}(\omega)\}$ is the real part of the Clausius-Mossotti factor and is defined as $$f_{CM}(\omega)=(\varepsilon^*_p-\varepsilon^*_m)/(\varepsilon^*_p+2\varepsilon^*_m), \quad (3)$$

where $\varepsilon^*_p$ is the complex permittivity of the particle and $\varepsilon^*_m$ is the complex permittivity of the suspending medium [Pethig 2010]. The complex permittivity is given by $$\varepsilon^* = \varepsilon - j\left(\frac{\sigma}{\omega}\right)$$

where σ is the real conductivity, ε is the real permittivity and ω is the frequency [Pethig 2010]. The real part of the Clausius-Mossotti factor is theoretically bounded between −½ and 1, which determines the direction and the relative strength of the DEP force. If the magnitude of $Re\{f_{CM}(\omega)\}$ is negative, then the particles are repelled from the electrodes and move towards a location where there is the lowest field gradient (negative DEP). Similarly, for positive values of $Re\{f_{CM}(\omega)\}$, particles are attracted to the electrode edges where there is the highest electric field gradient (positive DEP). However, for particles suspended in low conductivity buffers, at lower frequencies (<50 MHz), $f_{CM}$ is dependent on the medium ($\sigma_m$) and particle conductivity values ($\sigma_p$) [Pethig 2010]. $\sigma_p$ of the particle can be written as the sum of bulk conductivity ($\sigma_{pbulk}$) and surface conductivity (KS), which can be represented as $\sigma_p=\sigma_{pbulk}+(KS/r)$. Furthermore, for small particles (when r→0), $\sigma_p$ is dependent on the KS value [Hughes 1999, Ermolina 2005 and Basuray 2007].

A large DEP force is always desirable because it enables the development of high-throughput assays. Large electric field gradients $\nabla(|E|^2)$ are typically required to produce a large DEP force on molecules [Li 2002, Kim 2004]. Interdigitated electrodes (IDE) have been commonly used in the DEP experiments [Asbury, 2002]. IDEs have been used in high-throughput manipulation of biological cells and molecules [Li 2002, Zou 2007]. IDEs provide a simple electrode structure that generates the extremely high electric field gradients needed for DEP-based cell/molecule manipulation. In addition to IDEs, other electrode configurations like cusp-shaped nanocolloid assemblies have used in DEP experiments [Cheng 2010].

A number of nano-scale metal structures (e.g. Bowtie nano-apetures) have been successfully used in the context of plasmonic-based fluorescence detection. [Lu 2012, Mulvihill 2009, Maier 2005]. In addition to these planar nano-scale metallic structures, studies have used nano-capillaries in plasmonic-based fluorescently labeled nucleic acid detection [Čemažar 2016].

Low-cost, highly-sensitive, and minimally-invasive tests for the detection and monitoring of life-threatening diseases, such as cancer, will greatly reduce the worldwide disease burden [Murray 1996, Lopez 2006, Ezzati 2002]. Although conventional proteomic technologies have shown promise, their ability to detect disease progression from early to advanced illness stages is limited [Anderson 2002, Anderson 2005]. For example, there are no reliable, non-invasive detection assays currently available to diagnose pancreatic, ovarian, and lung cancers [Eguia 2012, Hingorani 2003, Huang 2010, Wei 2011]. However, if diagnosed early, surgical resection could achieve long-term control of these cancers [Eguia 2012, Hingorani 2003, Huang 2010, Wei 2011]. Studies have shown that blood-based microRNA (miRNA) is a sensitive biomarker for diagnosis of a large number of diseases, including early detection of cancers [Habbe 2009, Ganepola 2014]. This is largely because of the upstream positions of miRNAs in disease-promoting, regulation cascades [Habbe 2009, Ganepola 2014]. Also, it has been shown that miRNAs have exceptional stability in body fluids (e.g., blood and serum). Therefore, miRNA is a promising diagnostic biomarker for many diseases, including some cancers that are not currently being successfully diagnosed [Habbe 2009, Ganepola 2014]. More than a decade of research has identified miRNA panels that are differentially regulated during various disease states and subsequent stages of progression [Habbe 2009, Ganepola 2014]. To successfully translate these findings into a diagnostic test, there is a need for a procedure that can accurately, rapidly and with low-assay cost quantify miRNA targets from blood at point-of-care settings.

Quantitative real-time polymerase chain reaction (qRT-PCR) and next-generation sequencing (NGS) are the gold standards for miRNA detection in body fluids [Chen 2005, Varkonyi-Gasic 2007, Friedlander 2008]. NGS is costly (>$1000 per sample), has a slow turnaround time (days to weeks), is inefficient for detecting miRNAs, and lacks the ability to quantify low-copy-number miRNAs (below pM) [Chen 2005, Varkonyi-Gasic 2007, Friedlander 2008]. Therefore, NGS is not ideal for diagnosis. With respect to qRT-PCR, the detection of miRNA requires stable reference genes [Vomhof-DeKrey 2008], but identification of candidate reference genes in extracellular fluids is technically difficult and may be unique to each disease state [Vomhof-DeKrey 2008]. Furthermore, qRT-PCR reactions are expensive (approximately $2000 per clinical sample), time-consuming (>7 h) and thus unsuitable for routine testing [Chen 2005, Varkonyi-Gasic 2007, Friedlander 2008]. Other miRNA detection techniques include microarrays and electrochemical-, plasmonic-, and hybridization-based sensors. These techniques use diffusion of molecules or a combination of diffusion and sample flow to apply target miRNAs to detection electrodes or complementary capture molecules typically immobilized on solid surfaces or electrodes [Lodes 2009, Bettazzi 2013, Cissell 2009, Yin 2012, Lusi 2009]. Diffusion is not a selective or steady-state process and, therefore, produces results with a large degree of inter-sample variability, especially when used to detect picomolar or sub-picomolar concentrations. Additionally, molecular crowding near detection electrodes produces steric hindrance, which reduces sensitivity, limit of detection and sensing throughput making it difficult to detect molecules at pM concentrations [Roy 2011]. To minimize molecular crowding, researchers dilute serum samples, but this results in a significant reduction in the miRNA concentration available for detection. Due to the low abundance of target miRNA in early-stage disease, serum dilution can improve steric hindrance but at a cost in detection sensitivity.

External alternating-current (AC) potentials likely produce temperatures and electric fields in biological buffers resulting in thermophoresis (or thermophoretic diffusion), diffusion and dielectrophoresis (or dielectrophoretic force) on suspended macromolecules. The extent of the magnitude and direction of these interactions depends on the single versus double stranded nucleic acid structure [Chou 2002]. Therefore, detection of a specific miRNA species can be concentrated by this technology when hybridized to a fluorescent DNA probe, due to its double-stranded nature. It is further likely that the fluorescence enhancement of oscillating dipole fluorophores will harness energy from localized electric fields from scattered light. Dielectrophoresis can be used to place fluorophore molecules in the areas with large localized electric fields of scattered light, resulting in a modulation of fluorescence intensity.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The present invention relates to an apparatus and methods for an integrated dielectrophoretic (DEP) and surface plasmonic platform to quantify approximately 1 pM of fluorescent molecules in low conductivity buffers.

The present invention also relates to an apparatus and methods for an interdigitated array of microelectrodes with nano-scale plasmonic structures to quantify approximately 1 fM of fluorescent molecules in low conductivity buffers.

The present invention also relates to interdigitated electrode apparatus comprising: an array of interdigitated mesh electrodes; glass substrate; conductive metal; hotspots at the periphery of the apparatus; and a well for receiving biological samples.

In some embodiments of the present invention, the nanostructure of the interdigitated electrode apparatus is pearl or T-shaped.

In other embodiments of the present invention, the conductive metal is silver (Ag) or gold (Au).

Also described herein is a method for detecting biomarkers in a biological sample comprising: obtaining a biological sample from a subject; labeling a target biomarker molecule; adding the biological sample with labeled biomarker into an interdigitated electrode apparatus; applying a suitable DEP force to the apparatus; and measuring the amount of labeled biomarker in the biological sample.

In one embodiment of the methods described herein, the biomarkers are selected from protein, RNA, or DNA, or combinations thereof.

In other embodiments of the methods described herein, the biomarker is miRNA.

In some embodiments of the methods described herein, the biomarkers are labeled with fluorophores.

In further embodiments of the methods described herein, the biomarker is labeled with a fluorescent oligonucleotide sequence complimentary to the biomarker of interest.

In other embodiments of the methods described herein, the biomarker is labeled with an antibody.

In some embodiments of the methods described herein, the biological sample is blood, serum, plasma, saliva, or urine.

BRIEF DESCRIPTION OF THE DRAWINGS

FIG. 1(e) was used for this calculation. Scale bar indicates 200 nm. (c) Variation of the electric field gradient in the z direction. "X" indicates the z=100 nm plane and "Y" is the top plane of the hotspots. (d) Variation of the electric field gradient along the contour C-D (z=100 nm, FIG. 2(a)).

FIG. 9: shows fluorescence intensity (a.u.) for miRNA-Let-7a.

DESCRIPTION OF EXEMPLARY EMBODIMENTS

Figure 1:
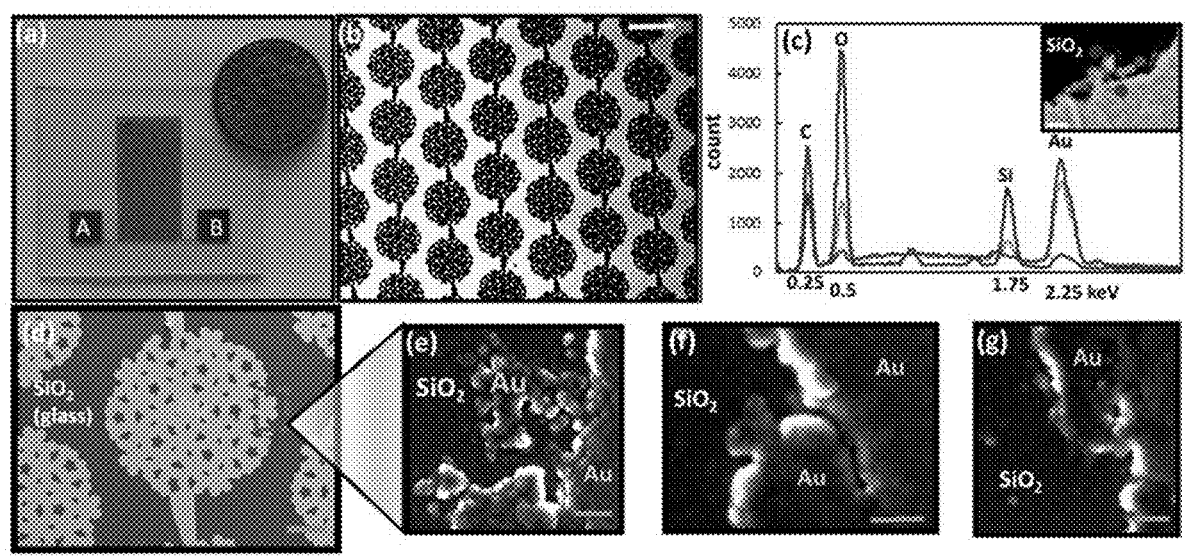
FIG. 1: Fabrication and characterization of PIDEs and hotspots for fluorescence experiments. (a) Final version of an embodiment of the present invention used in experiments. External electric potential was applied at A and B. (b) Close-up view of the PIDE array showing how PIDEs are designed and fabricated (scale bar 200 µm). (c) Characterization of the hotspots using an energy dispersive spectroscope (EDS). The hotspot shown in the inset was characterized using EDS and spectra are shown in the figure. Scale bar of the inset 100 nm. (d) Characterization of the hotspots using SEM. Low magnification view of a PIDE (scale bar 50 µm). (e, f and g) The SEM images showing hotspots of various sizes and shapes (scale bars 200 nm).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a biomarker" includes a plurality of such biomarkers, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, width, length, height, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term RNA molecules include any suitable double-stranded or single stranded RNA molecules, such as, but not limited to, messenger RNA (mRNA), small interfering RNA (siRNA) and/or microRNA (miRNA), or their single stranded counterparts.

As used herein, the term "biomarker" includes any protein, peptide, nucleic acid oligomer, antibody, or small molecule associated with a disease or pathology or a risk for developing a disease or pathology.

The presently-disclosed subject matter includes methods and products for detection of RNA. In one embodiment, the product includes an RNA-label conjugate. In another embodiment, the RNA-label conjugate is directly conjugated to nano-hotspots.

The present invention relates to an apparatus and methods for an integrated dielectrophoretic (DEP) and surface plasmonic platform to quantify approximately 1 pM of fluorescent molecules in low conductivity buffers. Detecting extremely low-levels of fluorescently labelled biomarkers is important for the quantification of disease related biomarkers in biological samples such as blood, serum, plasma, saliva, or urine to understand important biological states of a disease.

It is a highly-sensitive, low-cost, high-throughput biosensor device to quantify low-levels of biomarkers in biological samples. The underlying detection is based on integrated dielectrophoretic and plasmonic based fluorescence enhancement.

There are several aspects of the present invention. First is a method to measure biological molecules in very minute amounts. The biological molecules can be proteins, mRNA or DNA. A preferred mRNA is micro RNA (also known as miRNA). The biological molecules can be obtained from any animal tissue or biological fluid, preferably a body fluid from a patient in order to diagnose a disease. By measuring minute amounts of the relevant biological molecule, early stage onset and/or progression of a disease can be diagnosed. Using a panel of biological samples or measuring a panel of biological molecules can more specifically diagnose disease such as subtypes of disease or specific polymorphisms associated with a disease.

Once the biological sample has been obtained, it can be purified to eliminate non relevant biological molecules. For example, if one is trying to identify one or more particular miRNA, non RNA molecules could be removed. Likewise, if one is trying to identify one or more particular protein, non-protein molecules could be removed.

The method aspect of the invention comprises exerting a large DEP force on molecules while at the same time producing hotspots for the detection of molecules using plasmonic effects.

One embodiment of the present invention is directed towards a method for detecting biological molecules from a biological sample comprising: obtaining a biological sample; adding a labeling reagent to the biological sample; adding the labeled biological sample onto an apparatus; applying a suitable DEP force to a PIDE or TIAM apparatus; measuring the amount of labeled biological molecule in the biological sample.

In other embodiments of the presently disclosed methods, the biological molecule is selected from protein, RNA, or DNA.

In further embodiments of the present-invention, the labeling reagent is a fluorescently conjugated probe.

In other embodiments, the fluorescent probe is a oligonucleotide sequence complimentary to the biological molecule of interest.

In certain embodiments, a blood sample from a patient is obtained; miRNA is isolated via column chromatography; miRNA is hybridized with a fluorescent complementary DNA probe; the miRNA-DNA sample is transferred to a PIDE or TIAM apparatus wherein the miRNA-DNA is concentrated, fluorescence is enhanced and the molarity is calculated.

The starting molarity of Avidin molecules used in experiments was 1 µM. Since the DEP force on protein molecules is significantly weaker than nucleic acids, a new electrode array was developed that produces large electric field gradients. This high electric field gradient produces large DEP force on protein molecules. Since the DEP force and plasmonic effects of fluorescently labeled protein molecules were integrated, there must be a simple and scalable electrode design and micro-fabrication method that allows the production of integrated metal structures with hotspots. Pearl-shaped Interdigitated Electrodes (PIDEs) for integrated DEP and plasmonic experiments were developed, tested and manufactured.

Since the positive DEP force concentrates particles near the electrode's edges where plasmonic hotspots are present positive DEP, was used in one embodiment.

One embodiment of the present invention that was designed and fabricated is a new electrode design (PIDE) that allows us to establish a large DEP force on molecules while at the same time producing hotspots using plasmonic effects to detect of molecules. The conditions for exerting the appropriate DEP force and producing hotspots is described in general and specific detail in Example 1 of this specification. Details for detecting proteins is found in Example 2 of this specification and details for detecting RNA is found in Example 3 of this specification.

Since DEP and plasmonic-based detection were used, traditional interdigitated electrodes (IDEs) or any other electrode configurations were not a viable solution for an apparatus or a method of the present invention. Therefore, PIDEs were designed and used. Pictures of the PIDE are shown in FIGS. 1(a, b and d). In comparison with traditional IDEs, PIDE electrodes are capable of generating higher electric field gradients $\nabla(|E|^2)$ than traditional IDEs. Typically, the PIDE electrodes are generating about two to three times higher electric field gradients than the traditional IDEs [Nawarathna 2009, Gupta 2012].

Since DEP and plasmonic effects are combined in the present invention the experiments using DEP force to place molecules on the hotspots, these plasmonic structures are not directly applicable to the experiments. Further, fabrication of those nano-scale metal structures requires sophisticated equipment (e.g. electron beam lithography) and nano-fabrication facilities.

Circulating microRNA (miRNA) molecules could potentially be used for early diagnosis of diseases such as cancer. However, one of the major hurdles of translating miRNA into diagnosis, is the inability to rapidly detect miRNAs with high-sensitivity and at an affordable cost. To address this need, described herein is the iLluminate-miRNA platform, which is comprised of T-shaped interdigitated array of microelectrodes (TIAMs), using the TIAMs to measure the fluorescent intensity variation with frequency of the electric field between hybridized RNA and control RNA. Compared to the current gold standard, qRT-PCR, the iLluminate-miRNA method successfully improved assay time, cost and sensitivity of miRNA detection. This was achieved using an approach that selectively concentrates fluorophore-labeled miRNA-DNA duplexes in plasmonic regions and significantly enhances the fluorescence intensity of these fluorophores. The results show that the detection limit of miRNA spiked into water or serum was about 1 fM, which significantly surpassed qRT-PCR. In summary, the iLluminate-miRNA platform is expected to be used for diagnostic purposes at point-of-care settings.

To address short comings of the prior art including but not limited to; high cost, slow turnaround time, inability to quantify low copy number miRNA, the dependence on reference genes, inter-sample variability, and molecular crowding, a new miRNA detection platform called iLluminate-miRNA has been developed.

The apparatus aspect of the invention performs the DEP and plasmonic excitement of the labeled molecules and the detection of the biological molecules of interest. The apparatus and the method for fabricating it are described in general and specific detail in Examples 1 and 4 of this specification. One embodiment of an apparatus utilizes a novel electrode design known as Pearl-shaped Interdigitated Electrode (PIDE). The conducting metal can be any metal capable of conducting electricity either AC and/or DC. The most preferred metal is Au or Ag.

The present invention is useful for the quantification of disease related biomarkers in biological samples such as blood, serum, plasma, saliva, or urine to understand important biological states of a disease. Currently the ELISA method is the gold standard for detecting/quantifying biomarkers in biological samples and it has a minimum detection limit of 250 pg of target biomarkers in 1 mL of sample. This detection limit is not sufficient to diagnose many diseases. Especially, in the early stage of disease development, it is required to detect/quantify biomarkers much lower than the current limit.

For example, pancreatic cancer (PC) is the fourth leading cause of cancer deaths. In 2015, PC accounted for approximately 50,000 deaths in the US [Beger, 2003, Miura, 2006, Goonetileke, 2007]. In the last decade, the prevalence of PC has steadily increased, making PC a major health concern in the US [Beger, 2003]. Current imaging-based diagnostic methods cannot detect PC at a treatable stage; therefore, it is unlikely that patients can be treated successfully. The failure of imaging-based detection is primarily due to the deep location of the pancreas in the body. Conventional imaging techniques cannot image the entire pancreas with sufficient resolution for diagnosis; therefore, alternative detection methods are needed. Currently, carbohydrate antigen 19-9 (CA199) is the only PC diagnostic biomarker approved by the FDA. However, the available CA 19-9 immunoassay lacks the sensitivity and specificity needed for accurate detection [Frebourg, 1988, Steinberg, 1990]. Previous studies have shown that various cancers, including PC, can be detected earlier using clinical blood biomarkers, such as microRNAs (miRNAs), DNA, and proteins [Mitchell, 2008, Loften-Day, 2008, Osman, 2006]. miRNAs are one of the most sensitive clinical blood biomarkers because they play a role in tumorigenesis and are stable in body fluids (e.g., blood, serum). Therefore, a miRNA biomarker-detection assay could be a promising diagnostic tool for many cancers, including pancreatic cancer (PC) [Mitchell, 2008, Kosaka, 2010]. Previous studies have identified panels of miRNAs, individual miRNAs, and combinations of CA 19-9 and miRNAs with diagnostic potential [Liu, 2012, Tricoli, 2007, Ganepola, 2014]. To successfully translate these findings into a diagnosis, miRNA targets in clinical samples need to be accurately quantified. In addition, this miRNA quantification technique needs to be straight-forward to perform in clinics, hospitals, and other point-of-care settings Current methods for detecting PC at a treatable stage in a point-of-care setting do not have the throughput, limit of detection, or sensitivity needed to be effective [Frebourg, 1988, Steinberg, 1990]. DEP and fluorescence enhancement are integrated to generate a quick, easy, high sensitivity, miRNA-based diagnostic tool. In an embodiment of the present invention, miRNA (target and non-target) is first isolated from the serum sample using a commercially available kit [Chen, 2008]. The entire length of the target miRNAs are selectively hybridized with a complementary DNA primer conjugated to a fluorophore [Roy, 2011]. The miRNA sample, composed of non-target miRNA, siRNA, hybridized miRNA-DNA duplexes, and free complementary DNA, will be transferred to a pearl-shaped interdigitated array of microelectrodes (PIAMs).

To address the issue of detect extremely low-levels of fluorescently labelled biomarkers integrated dielectrophoretic and plasmonic based fluorescence enhancement was used.

Also disclosed herein is an miRNA detection technique which comprises isolating miRNA from serum, hybridizing target miRNA with complementary DNA probes with fluorescent labels creating miRNA-DNA duplexes, and determining the molarity of miRNA in the serum sample.

Further disclosed herein is a method which produces greater recovery than the standard RT-PCR procedure for quantifying RNA from serum samples. Methods disclosed herein are also faster, more sensitive and more cost effective than RT-PCR protocols.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is further illustrated by the following specific but non-limiting examples. The following examples may include prophetic examples, notwithstanding the numerical values, results and/or data referred to and contained in the examples. The following examples may include compilations of data that are representative of data gathered at various times during the course of development and experimentation related to the present invention.

EXAMPLES

Example 1: Electrode Fabrication of PIDE

A new electrode design (PIDE) was designed and fabricated that allows us to establish a large DEP force on molecules while at the same time producing hotspots for the detection of molecules using plasmonic effects.

PIDEs were fabricated using standard microfabrication techniques. The details of the fabrication are published elsewhere [Pommer 2008]. Hotspots were produced in the periphery of the pearls of the PIDEs. The production of hotspots was achieved through careful over-exposing of photoresists films to UV light during the photolithography. The photoresist films were developed, sputtered 1000 Å Au and lifted off the photoresists film in acetone. This fabrication process produced a large number of hotspots with various shapes and sizes. A few of the shapes of the hotspots are shown in FIGS. 1(e, f, and g). This was a repeatable fabrication process that was used to produce hotspots in the present invention. The manufacturing process did not use the E-beam lithography tool. Further, production of hotspot is a part of traditional photolithography process. Therefore, production of large number of hotspots needed to accommodate clinical sample volumes (typically few milliliters) is technically possible.

To gain a deep understanding on how the integration of DEP and hotspots potentially enhance the surface-plasmonic effects, the scanning electron microscope (SEM) was used to image the locations of the hotspots and energy dispersive spectroscope (EDS) to perform an elemental analysis of the hotspots [Nawarathna 2013]. The SEM images were used to measure the dimensions of the hotspots (see FIGS. 1(d, e, f, and g)). However, SEM images do not provide detailed elemental characterization of hotspots (locations of metals and dielectrics). For example, for the SEM image shown in FIG. 1(c), the EDS was used to find out if there is a residual photoresists films or any other metallic or non-metallic contaminations are still remaining in the hotspot (indicated in blue dot). These contaminations will be visible in the EDS spectrum. The "point-and-shoot" technique in the EDS software was used and the elements present in the hotspots were determined. A typical result of an EDS analysis of a hotspot is indicated in the FIG. 1(c). Note that if the positive DEP-placed biomarker molecules on the dielectric material is between gold electrode (lower dot) and the gold arm (upper dot), it will be subjected to surface plasmonic effects.

To quantitatively understand the electric field gradient, $\nabla(|E|^2)$, generated by the PIDE structures, the AC/DC module of commercially available COMSOL (COMSOL, Inc.) software was used and the expected electric field gradients calculated. In this calculation, the PIDE were first drawn to scale using AutoCAD (Autodesk) software and then imported into the COMSOL software. It was then assumed that a buffer solution ($\sigma$=0.03 S/m and $\varepsilon_r$=80.3) filled the space above the electrodes. The swept mesh technique was used to mesh PIDE electrodes. This is needed to properly mesh nano and micro scale features of the electrodes. First, the x-y (z=0) plane of the electrode is meshed using "Free Triangular Mesh" with maximum element size 90 nm and minimum element size 1 nm. The "Free Triangular Mesh" was then swept in z direction with minimum and maximum mesh size of 5 nm and 1 nm respectively. This procedure allowed us to successfully mesh the electrodes. Further, it was assumed that an external potential with a frequency (120 kHz) and voltage (1 Vpp) was applied to the electrodes. This is the AC potential used in the DEP experiments. 120 kHz was chosen because it has been reported that the positive DEP force will be maximum at 120 kHz for biomarker molecules [Nawarathna 2009]. Finally, the electric field from which the electric field gradient was extracted in the vicinity of the PIDE structures was calculated.

Figure 2:
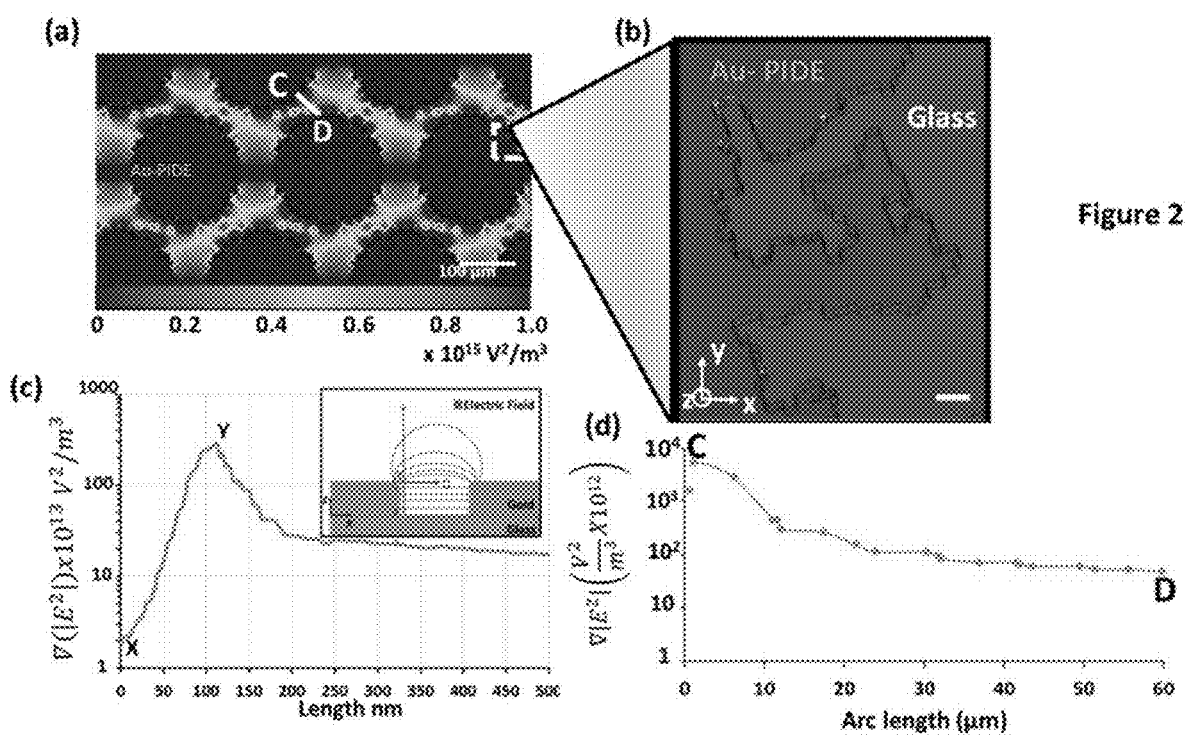
FIG. 2: Calculated electric field gradients ($\nabla(|E|^2)$) near the electrodes and hotspots. (a) Calculated electric field gradients on the PIDEs in the x-y plane (z=100 nm) (b) Close-up view of the electric field gradient of hotspots in z=100 nm plane.
Figure 3:
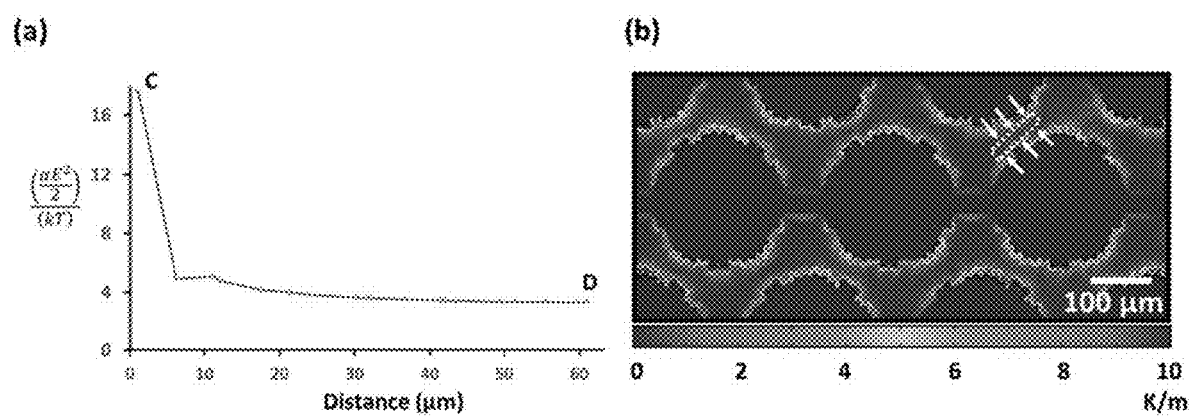
FIG. 3: Comparison of energy harvested by biomolecules from AC electric field to ground state energy and thermophoretic effects on molecules. (a) Comparison of energy harvested from the electric field to ground state energy. Note that almost all molecules that are in the sample harvest at least four times more energy than the ground state energy. (b) Calculation of the temperature gradient near electrodes. This temperature gradient will produce thermophoeretic forces on molecules on biomolecules.

In FIG. 2(a), the calculated electric field gradient in the x-y plane is shown (z=100 nm) of the PIDE electrodes. There are high and low electric field gradient regions in the PIDE, darker regions have the lowest electric field gradient (approximately $10^{12}$ $V^2/m^3$) and lighter regions have the highest electric field gradients (approximately $3\times10^{15}$ $V^2/m^3$) [Nawarathna 2009]. The variation of the electric field gradient along the contour C-D was then calculated (FIG. 2(d)). According to this calculation, in comparison, the DEP force is only about 70-80 times smaller at 60 μm (point D) than the DEP force at point C. To further understand the DEP-assisted molecular placing in the hotspots, the energy ($\frac{1}{2}\alpha E^2$) provided by the external electric field to the molecules was calculated. The electric energy with the ground state energy of the molecules was then compared (kT; k is the Boltzmann constant; T is the average temperature on the electrodes). For the DEP force to be effective, the energy provided by the external electric field must be greater than the ground state energy of the molecules. For comparison, these energies along the contour C-D were calculated, and results are shown in FIG. 3(a). Since the energy provided by the electric field is larger than the ground state energy, it can be concluded that positive DEP will bring molecules from 50-60 μm away from the interface and place molecules on the hotspots for quantification through surface plasmonic effects. Since this calculation shows the variation of $\nabla(|E|^2)$ in the x-y plane (along the contour C-D), another calculation was performed to find the variation of $\nabla(|E|^2)$ in the z direction. The $\nabla(|E|^2)$ in the z direction will produce DEP force on molecules in the z direction. The formula (above)

was used and the energy provided to the molecules by the electric field was calculated. the energy of the molecules was then compared to the ground state energy of the molecules. The calculation shows that, at z=500 nm (x=y=0), energy provided by the electric field is about 4 times greater than the ground state of the molecules. Therefore, the electric field gradient in the z direction will produce a sufficiently large DEP force to bring molecules from the z direction and combine with DEP in the x-y plane to place molecules in the hotspots. Furthermore, molecules that are far away from electrodes (z>>500 nm) will not be capable of using the DEP force to get trapped in the hotspots. One can use other forces such as electrophoretic force to bring those molecules closer to the electrodes so that DEP force will be strong enough to place them in the hotspots. Another option is to design the height of the channel within the DEP active area. Then DEP force will be sufficient to trap all the molecules in the hotspots. FIG. 2(b) illustrates the variation of $\nabla(|E|^2)$ in the z=100 nm plane and FIG. 2(c) shows the variation of $\nabla(|E|^2)$ in the x-z plane. From these analyses, it can be concluded that highest $\nabla(|E|^2)$ is generated at the top edge of the hotspots (FIG. 2(c)). Therefore, these top edges (indicated as "Y" in the FIG. 2(c) will have a large number of molecules collected through DEP. This analysis agrees with the experimental results in FIG. 5(a) inset, where it was observed that the concentrating molecules at the top edges of the hotspots.

Figure 4:
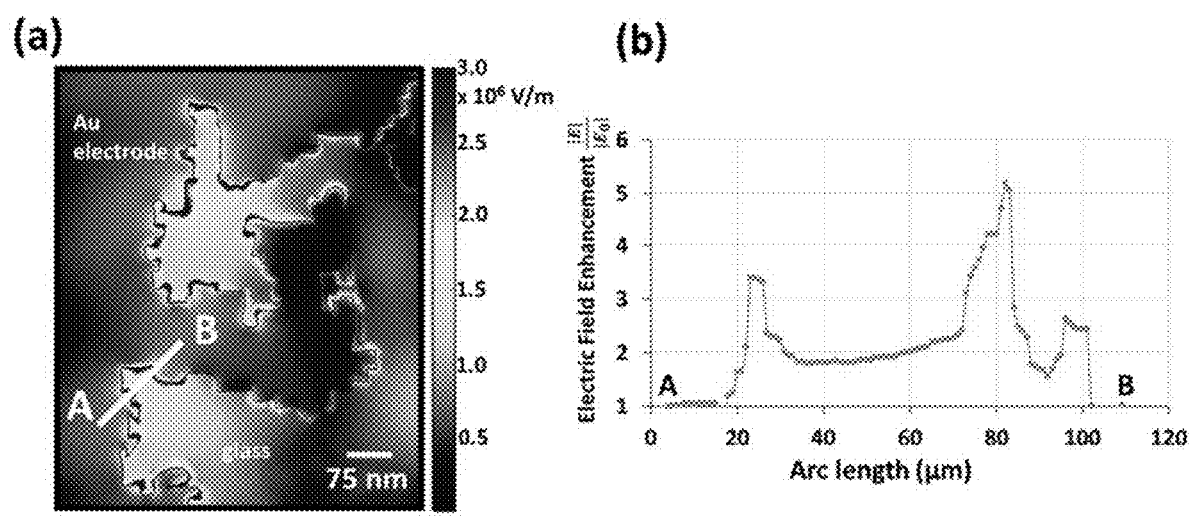
FIG. 4: Calculated electric enhancements due to the plasmonic effects. (a) The SEM image of the FIG. 1(e) and the COMSOL software was used to calculate the expected electric fields in the sample when 1 mW light was applied perpendicular to the sample. (b) Calculated the electric field enhancement along the contour A-B of the FIG. 4(a). This demonstrates the typical electric field enhancement that is expected from the hotspots. $E_0$ is the electric field that is away from the hotspots.

Next, another COMSOL calculation was performed to find the expected electric field enhancement near hotspots from the plasmonic effects. This electric field enhancement is expected when the fluorescent biomarker molecules is excited using the appropriate light source. To perform the calculation, first the hotspots were drawn in AutoCAD software using a SEM image of the actual hotspots (FIG. 1(e)) and imported into the COMSOL software. Then the wave optics module of the COMSOL software and solved the traditional wave equation were used. In this application, when it is assumed the electric field as a planar traveling wave, the wave equation transforms into equation (2). COMSOL software solved the equation (2) and calculated the expected electric field distribution and electric field enhancement near hotspots.

$$\nabla \times \mu^{-1}(\nabla \times E) - k_0^2\left(\epsilon_r - \frac{j\sigma}{\omega\epsilon_0}\right)E = 0 \quad (2)$$

Where E is the electric field, µ=permittivity, $k_0$=wave number, σ=electric conductivity, $\epsilon_r$=relative dielectric constant, $\epsilon_0$=dielectric constant of air, ω=angular frequency. It is also assumed that hotspots were made out of Au and a transverse electric wave with 500 nm wavelength and 1 mW power passing through the hotspots. A 500-nm wavelength was chosen because it is close to the actual excitation wavelength that was used in exemplary embodiments. FIG. 4(a) indicates the electric field distribution near hotspots. There is large electric field near hotspots. Published literature has been shown similar electric field distribution near metallic nanostructures [Iandolo 2013]. For comparison, the electric field variation across the contour A-B was calculated. This will also provide good understanding of how the electric field varies across the hotspots. The contour A-B goes across a number of hotspots and FIG. 4(b) shows the electric field enhancement across A-B and the maximum electric field enhancement near the hotspots is about six-fold. Most of the published literature has reported about a three-fold electric field enhancement [Fu 2010]. This electric field enhancement directly contributes to the fluorescence of Avidin molecules. Studies have shown that enhanced electric fields increase the fluorescence emission of Avidin molecules through "Lightning Rod Effect" [Geddes, 2002]. In addition, the plasmonic hotspots decrease the radiative decay rate of the fluorophore and therefore lifetime of the fluorophore will have a reduction [Geddes, 2002]. Through this characterization, the abilities of electrodes to generate DEP and plasmonic effects is apparent.

In this high electric field and its gradients, there can be significant Joule heating resulting in a temperature increase near the electrodes. If the temperature is too high, the molecules that are being detected will be exposed to the high temperature and lose their functionality. To understand the Joule heating in the PIDE electrodes, the temperature increase ($\Delta T=(T_{actual}-T_{room})$; $T_{room}=300K$) was calculated in the PIDEs using COMSOL software. First, the electrical energy supplied to the surroundings through PIDEs was calculated. It is assumed that electrical energy is converted to the thermal energy through the temperature increase. Through this calculation, there is a roughly 2° temperature increase (above the room temperature) will take place during the experiments, and this temperature will not cause any damage to the molecules. This result (temperature increase) can be deduced from the published work by others [Nakano 2014, Chaurey 2013, Lu 2015]. In addition, under this temperature distribution, one expects thermophoretic force (TP) on molecules through thermophoresis. The TP force on molecules causes thermodiffusion, (j) mathematically represented as, $$\vec{j}=-D_T c \nabla T \quad (3)$$

Figure 8:
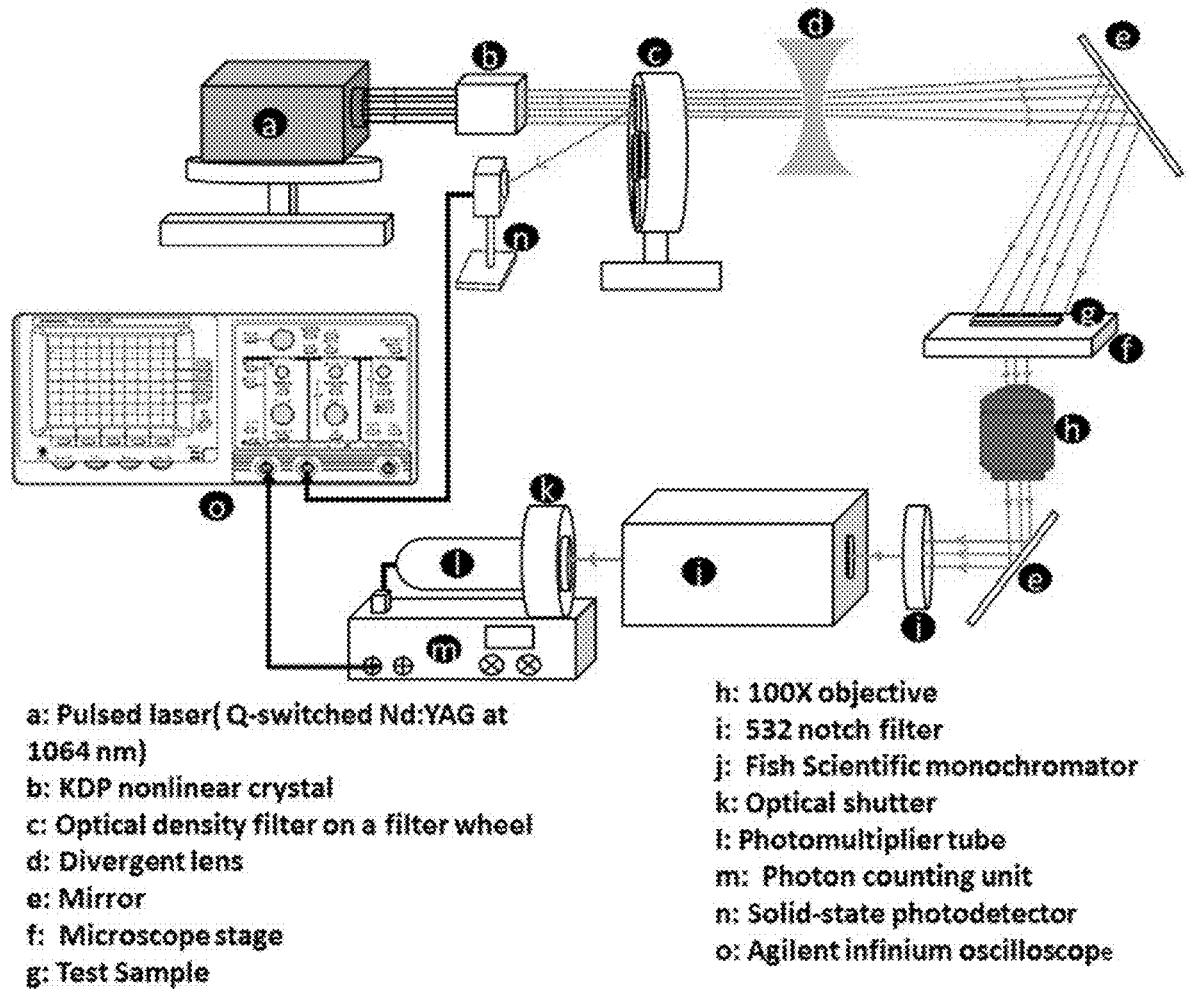
FIG. 8: Illustrates the experimental set-up used for measure lifetime of molecules

$D_T$ is the thermophoretic mobility, c is the concentration of molecules and $\nabla T$ is the temperature gradient. According to the equation (3), the TP will push the molecules away from the places where there are high temperature gradients. To further understand the motion of molecules through TP, the temperature calculation was extended and $\nabla T$ determined. FIG. 3(b) indicates the variation of $\nabla T$ on the sample. The thermodiffusion will push the molecules away from the electrode boundaries to the region indicated in the white box in the FIG. 3(b). At the same time, DEP will attract the molecules toward the electrode boundaries (FIG. 2(a)). If the electrodiffusion is dominant, there must be an accumulation of molecules in the area indicated by the white rectangle (FIG. 3(b)). However, in experiments, accumulation of molecules in that area was not observed (FIG. 5(a) inset). Therefore, it can be concluded from these calculations that the effect of the electrodiffusion is not significant. Next, experiments as outlined in FIG. 8 were conducted where the fluorescence and lifetime of the target biomarker molecules were measured.

Example 2: Detection of Proteins

Figure 5:
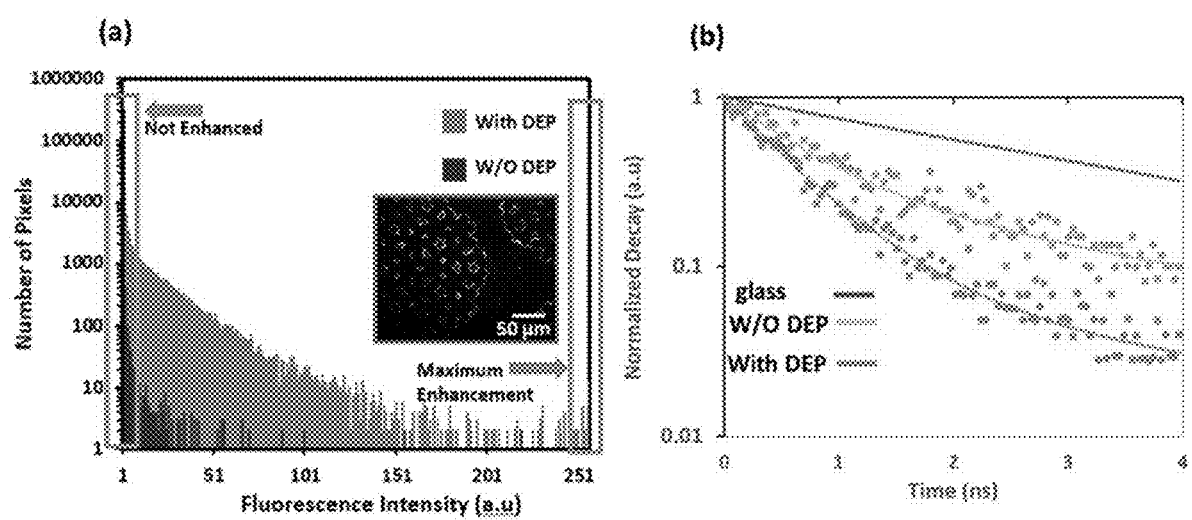
FIG. 5: The comparison and contrast of the effects of DEP in quantifying molecules using surface plasmonic effects. (a) Comparison of the fluorescence measured from a sample with and without DEP. Note that sample with DEP concentrate the Avidin molecules near the electrode edges and increase the fluorescence. Similarly, sample that has no DEP, randomly scatter the molecules. Inset shows the picture of the sample with DEP used to generate the above plot. Further, the pixels are indicated where there are no plasmonic effects as well as where there are significant plasmonic effects. (b) Fluorescence decay curves for the TRITC labeled biotin molecules in glass coverslip, on electrodes with DEP and on electrodes without DEP. These decay curves were used to calculate the lifetimes of the molecules in each case.

To experimentally demonstrate how will the integration of DEP and plasmonic effects enhance the detection of biomarker molecules, fluorescently labeled Avidin molecules were used (size: 68 kDa; ex: 500 nm, em: 515 nm; suspended in a buffer that has a conductivity of 0.03 S/m; Vector laboratories Inc, Burlingame, Calif.,) as the molecules of interest. Published literature reports have used similar molecules such as BSA and IgG molecules to show their proof of concepts [Fu 2010, Barik 2014]. Published reports that utilize only plasmonic effects have reported detecting about 1 µM [Fu 2010]. To demonstrate the quantification of low concentrations of Avidin molecules, approximately 1 pM Avidin molecules were used in experiments. To find the optimum frequency of the electric field (positive DEP force) that can quickly bring molecules and place them in hotspots, the frequency was varied from 50 kHz-500 kHz and the number of Avidin molecules collected near the electrodes was measured. Briefly, for each frequency, a fluorescence picture of the electrodes with molecules and measured the fluorescence intensity at the periphery of electrodes was recorded. The frequency that generated the highest fluorescence (120 kHz) was selected. That frequency was used for the experiments involving Avidin molecules. In experiments, 1 pM Avidin molecules were pipetted onto PIDEs and an electric field (10 Vpp with 120 kHz) was applied to the terminals A and B (FIG. 1(a)) to concentrate Avidin molecules on the hotspots. The electric field was kept on (active) for 2-3 minutes to positive DEP to place molecules in the hotspots. The electric field was then turned off and the PIDEs were imaged using a low-power fluorescent microscope and the fluorescence image was recorded (inset of FIG. 5(a)). The electric field was turned off to avoid any interference from the electric field during fluorescence microscopy. After turning off the electric field, a fluorescence image was instantly recorded (<5 seconds). Since the DEP off time is very short, Avidin molecules did not move away from hotspots during the fluorescence measurements. Further, the Avidin molecules that are extracted by positive DEP near the electrodes do not scatter out immediately after turning off the DEP force. To compare the effects of DEP concentrating biomarker molecules in hotspots, an experiment was conducted using another PIDE array without applying DEP. Finally, using a custom made software program, the fluorescent intensity of each pixel of each image was extracted and plotted for comparison. FIG. 5(a) illustrates the fluorescence intensity vs. the number of pixels for the two experiments discussed above. By simple comparison, there is a large-number of bright pixels in the sample with DEP (light grey) when compared with the same sample that had no DEP (dark grey). Therefore, it is assumed that DEP effectively concentrated the biomarkers on the hotspots and biomarker molecules in the hotspots are subjected to plasmonic effects and produce high fluorescence signal. Further, in FIG. 5(a), the pixels are indicated, where there are no plasmonic effects as well as where there are significant plasmonic effects. If DEP place molecules in the hotspots, those molecules must have a significant reduction on the fluorescence lifetime. To experimentally show this, fluorescence lifetime spectroscopy was used.

The purpose of measuring the lifetime is based on the belief, given teachings in the art, that the biomarkers in the hotspots will have a significantly shorter fluorescence lifetime than the biomarkers that are not under the influence of the plasmonic effect. There are a number of methods available for measuring fluorescence lifetimes [Brismar 1995]. Time-correlated single photon counting (TCSPC) is commonly used in many applications in which exponential decay of fluorescence light intensity is measured and used to calculate the lifetimes [Brismar 1995]. The detailed procedure for calculating the lifetime of a sample is published elsewhere [Brismar 1995]. To measure the lifetimes of molecules that are placed in the hotspots, 150 nM, Tetramethylrhodamine (TRITC) labeled streptavidin molecules were used (ProteinMods, Madison, Wis.). The fluorescence lifetime of streptavidin TRITC was measured using the TCSPC system designed and assembled accordingly, the TCSPC system consists of following parts: A Teem Photonics Microchip NanoPulse NP-10820-100 Nd:YAG laser at 1064 nm with 590 ps of pulse duration, 100 of energy per pulse, and 6.9 kHz of pulse-repetition rate, a KDP nonlinear crystal to convert the laser output to 532 nm through second harmonic generation, a Zeiss Axiovert 40 C microscope with an 100× objective, an Ocean Optics 532 nm notch filter, a Fisher Scientific monochromator tuned at 572 nm with an full-width at half maximum bandwidth of 8 nm, a Hamamatsu photomultiplier tube R7207-01 powered by an 800 V source, a Hamamatsu photon counting unit C6465, an Agilent infinium 54853A DSO oscilloscope with 20 Gsa/s, and a photodiode Electro-Optics ET-2040.

The TRITC labeled streptavidin molecules were suspended in 0.01× phosphate buffered saline (PBS) buffer and pipetted about 100 μL of streptavidin over the electrodes and applied an external electric field (using electric potential of 10 Vpp and 400 kHz) and placed the molecules on the hotspots. As before, the electric field was applied and left it on for 2-3 minutes for fluorescent molecules to experience DEP and move to hotspots. The selection of frequency (400 kHz) and voltage (10 Vpp) was chosen to generate the highest DEP force on TRITC molecules. To find the frequency and voltage, 120 kHz and 1 Vpp was the starting parameters and the frequency and voltage were gradually increased and observed the motion of TRITC molecules. At 400 kHz and 10 Vpp, these molecules experienced the largest positive DEP force. The DEP was then turned off and measured the photons that emit from the sample with time. These values are represented as points in the FIG. 5(b). Next, using the photon vs. time, the fluorescence decay of TRITC labeled streptavidin with time was calculated. Finally, the least squares algorithm was used to calculate the amplitude and the decay coefficient of the two exponential components of the fluorescence decay of TRITC that best fit the data obtained with the TCSPC system in samples that have the metal-glass interface without DEP, and the metal-glass interface with DEP. The only difference between these two samples was the DEP and all other experimental parameters were kept unchanged. The goodness of each fit was calculated using R-square and values were 0.976 and 0.979 for the sample with DEP and without DEP respectively. The equations with the respective coefficients in the metal-glass interface are:

$$I_{wDEP}(t)=0.92e^{-1.67t}+0.08e^{-0.25t},$$
$$I_{w/oDEP}(t)=0.75e^{-1.38t}+0.25e^{-0.25t}. \quad (4)$$

The Equations ($I_{w/oDEP}$ and $I_{wDEP}$ that denote fluorescence intensity without and with DEP respectively) in (4) are plotted in FIG. 4(b). The second exponential component in both equations has a decay coefficient (0.25 and 0.24) whose inverse is consistent with the reported fluorescence lifetime of conjugated TRITC [Brismar 1995]. The first exponential component in both equations had decay coefficients (1.67 and 1.38) whose inverse is close to the duration of the pulses from the Q-switched laser. Previous studies indicated the fast exponential decay, which is due to the surface plasmonic effect [Brismar 1995]. The lifetime of the sample that underwent positive DEP is $$\left(\frac{1}{1.67}=0.6\right)$$

is 0.6 nanoseconds and the lifetime of the sample without positive DEP is $$\left(\frac{1}{1.38}=0.72\right)$$

is 0.72 nanoseconds. This reduction in lifetime is due to the DEP concentrating streptavidin molecules in the hotspots.

Furthermore, the laser that was used in the example lifetime studies was a pulsed laser with pulse duration of 0.56 nanoseconds of full-width at half-maximum. Therefore, the lifetimes that are smaller than the 0.56 nanoseconds are not recorded. The purpose of the lifetime experiments was to demonstrate that the sample that underwent positive DEP would have reduction in lifetime compared to the sample that did not undergo DEP.

Finally, the molarity of Avidin molecules was varied from 1.5 µM to 15 fM and recorded an image for each molarity. The variation of fluorescence intensity versus number of pixels was plotted. It was assumed that fluorescence intensities that were above 80 were significant and above the white noise level. According to this criteria, the integrated dielectrophoretic and plasmonics based technique is capable of detecting about 1.5 pM of Avidin molecules.

Figure 7:
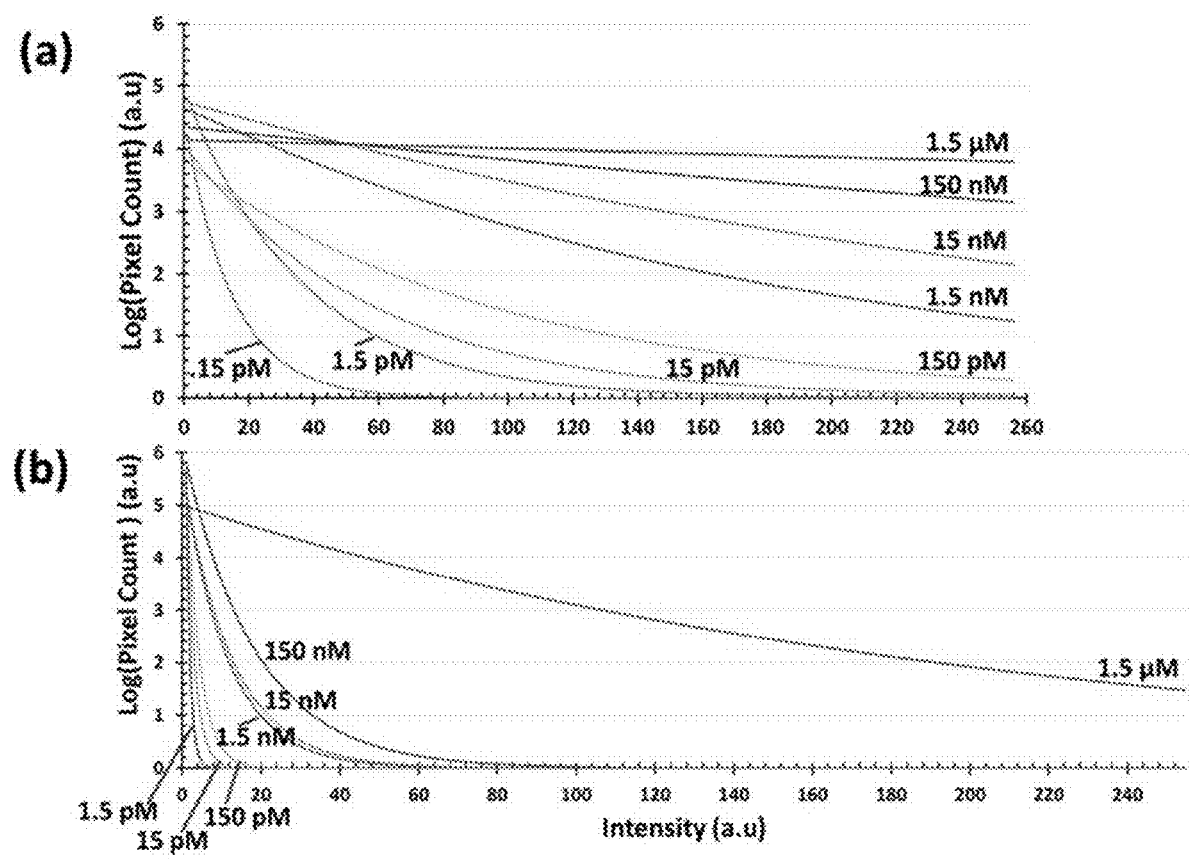
FIG. 7: Comparison of integrated dielectrophoretic and plasmonic based detection with standard fluorescence based detection. Variation of fluorescence versus molarity of the Avidin molecules (a) integrated dielectrophoresis and plasmonic based detection (b) standard fluorescence based detection.

To compare results and find the improvement in the detection, standard fluorescence techniques were used and the experiments repeated. Briefly, about 100 µL of Avidin molecules were pipetted (with varied molarities from 1.5 µM to 150 fM) and a fluorescence image of the sample was recorded for each molarity. The variation of fluorescence intensity versus number of pixels for each molarity was then plotted. Results are included in FIG. 7. It is assumed that fluorescence intensities that are above 80 is a valid intensity that is above the white noise level. According to the assumption, 1.5 µM is the smallest molarity that can be measured using the standard fluorescence. Therefore, by simple comparison (1.5 µM/1.5 pM=1,000,000-fold) the integrated dielectrophoretic and plasmonics based technique enhance the detection of Avidin molecules by about million fold.

Example 3: Detection of miRNA

Figure 6:
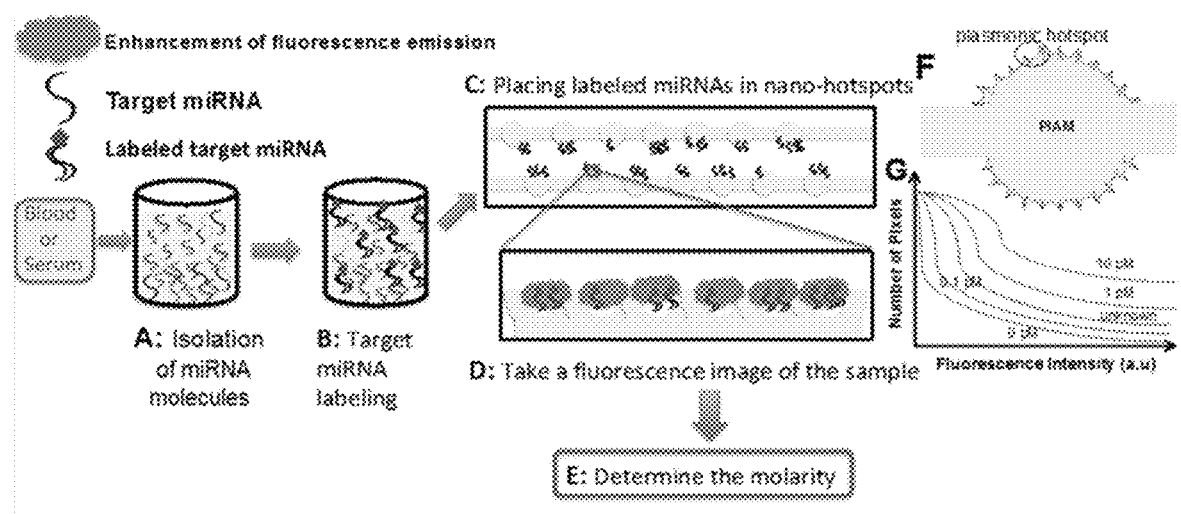
FIG. 6: Schematic Representation of an embodiment of Proposed miRNA Detection

FIG. 6 shows a schematic of the steps of the proposed technology. To overcome some of the shortcomings in the prior art, the following three steps were optimized. First, the frequency of DEP force needed to selectively extract miRNA-DNA duplexes and place them in plasmonic hotspots is isolated (step C). Second, the conditions needed to achieve maximum fluorescence enhancement of molecules in the plasmonic hotspots is determined (step D). Third, a simple method for calculating the molarity of the target miRNA in a sample is established (step E). The performance (limit of detection and recovery) of the proposed technology with RT-PCR was compared. Steps A and B are well established in the literature and widely used in clinical laboratories. Two common PC miRNA targets were selected, miR-642b and miR-22 for the experiments and miR-21 for negative control [Ganepola, 2014, Lee, 2007]. miRNA targets are synthesized through a commercial vendor. Every experiment will be performed for each miRNA separately. The steps are outlined below.

In an exemplary method, miRNA (target and nontarget) is isolated from the serum sample using a commercially available kit [Chen, 2008]. The entire length of the target miRNAs is selectively hybridized with a complementary DNA primer conjugated to a fluorophore [Roy, 2011]. The miRNA sample, composed of non-target miRNA, siRNA, hybridized miRNA-DNA duplexes, and free complementary DNA, is transferred to a pearl-shaped interdigitated array of microelectrodes (PIAMs). Approximately 500 nanoscale plasmonic hotspots are located at the periphery of each pearl. A small AC electrical signal (1-10 Vp-p) at a specific frequency will be applied. This applied electric field will generate a DEP force that selectively attracts hybridized miRNA-DNA duplexes to the hotspots. The frequency of the electric field will be optimized to selectively apply the DEP force to target miRNA-DNA duplexes based on their double-stranded characteristics (details discussed below) [Chou, 2002, Asbury, 2002]. Therefore, target miRNA-DNA duplexes will be attracted to and trapped in nanoscale plasmonic hotspots. Because all other molecules in the sample are single stranded, they experience repulsive or no DEP force, allowing them to be washed away from the electrodes [Chou, 2011, Gacoyne, 2002]. repulsive DEP is then used on miRNA-DNA duplexes to move molecules away from electrode edges. This step is needed to maximize plasmonic effects (described in the Methods). Finally, fluorophores are excited, and the plasmonic effects of the hotspots significantly enhance the fluorescence emission of miRNA-DNA duplexes. The sample is imaged and a simple scheme is developed to find the molarity of the target miRNAs. This method is high-throughput, with an estimated time to results of approximately 2 minutes, and low-cost because the manufacturing cost of the electrodes ranges from $5 to $10. From a technical standpoint, this method can detect even a few molecules and the DEP only attracts miRNA-DNA duplexes to the plasmonic hotspots, making it highly sensitive and specific, respectively [Lakowicz, 2001]. These factors combined will make the miRNA-based PC detection ideal in point-of-care settings. Therefore, the proposed research will fundamentally change how clinicians screen and treat patients with PC. Further, this technique can easily be translated to detect antigens and proteins. To detect those molecules, it is necessary to selectively label target molecules with fluorophores and determine the frequency of external electric field that generates the appropriate DEP force [Kawabata, 2001]. Further, this technique can easily be scaled up to simultaneously detect/quantify a biomarker panel with a large number of miRNA/antigens.

To overcome problems in the prior art, the following steps may be taken. First, the frequency of DEP force needed to selectively extract miRNA-DNA duplexes and place them in plasmonic hotspots is isolated (step C). Second, the conditions needed to achieve maximum fluorescence enhancement of molecules in the plasmonic hotspots is determined (step D). Third, a simple method for calculating the molarity of the target miRNA in a sample is used (step E). The performance (limit of detection and recovery) of the proposed technology with RT-PCR is also compared. Steps A and B are well established in the literature and widely used in clinical laboratories. Two common PC miRNA targets, miR-642b and miR-22 were selected for experiments and miR-21 for negative control [Ganepola, 2014, Lee, 2007]. miRNA targets are synthesized through a commercial vendor. Every experiment is performed for each miRNA separately. An embodiment of the method is discussed below.

Step A: miRNA isolation from serum samples. There are several miRNA isolation kits for serum samples available through commercial vendors. Typical isolation time is approximately 15 minutes per sample. Isolating RNA typically involves using RNA-binding beads to extract miRNA from the serum sample [Chen, 2008]. Commercially available isolation kit was used to isolate miRNAs (including target and non-target) from a 1 mL of serum sample. Commercially available Sigma-Aldrich mirPremier-microRNA Isolation Kits were used, (catalog number: SNC50). Steps are:

1: 1 ml of Lysis solution mix was prepared by adding 700 µL of ac microRNA Lysis Buffer (M1070), 300 µL of Binding Solution (L8042) and 10 µL of 2-mercaptoethanol solution. Then the lysis solution was mixed thoroughly for about 2 minutes in the vortex machine.

2: 1 mL of prepared lysis solution was added to the 1 mL of serum sample. Then, the mixture was gently mixed by slowly shaking the tube by hand. Mixture was left in a tube rack in room temperature for about 10 minutes.

3: The mixture was centrifuged at the speed of 14,000×g for 5 minutes to remove genomic DNAs, and large RNAs. Then the supernatant was transferred to a new 2 mL tube.

4: 700 μL of the supernatant mixture transferred into a Binding Column (red retainer ring) and centrifuge at maximum speed 14,000×g for 30 seconds. The flow-through liquid was decanted and repeated the binding step with the remaining mixture.

5: 700 μL of 100% ethanol was added into the column. Then centrifuged at maximum speed 14,000×g for 30 seconds.

6: Binding Column was transferred into a fresh Collection Tube. Then 500 μL of the Ethanol-diluted Wash Solution 2 into the column was added. Then centrifuged at maximum speed 14,000×g for 30 seconds. Discarded the flow-through liquid and return the column to the Collection Tube.

7: Another 500 μL of the Ethanol-diluted Wash Solution 2 was added into the column and centrifuged at maximum speed 14,000×g for 30 seconds. Discarded the flow-through liquid and return the column to the Collection Tube.

8. Centrifuged the column at maximum speed 14,000×g for 1 minute to dry. Carefully removed the column-tube assembly from the centrifuge to avoid splashing the residual flow through liquid to the dried column.

9. Transferred the column to a new 2 mL Collection Tube. 50 μL of Elution Solution (0.01× TE buffer) was directly added onto the center of the filter inside the column. Closed the cap and let the tube sit for 1 minute. Centrifuged at maximum speed 14,000×g for 1 minute to elute. Repeated the elution step by collecting the elute in a pipette tip and reload the solution directly onto the center of the filter inside the column. Close the cap and let the tube sit for 1 minute. Centrifuge at maximum speed for 1 minute to elute.

10: The eluted solution was used in experiments.

Step B: Hybridization of target miRNA with complementary DNA probes with fluorophore tag. Target miRNA is selectively hybridized with fluorescently labeled 24-mer DNA molecules. Hybridization conditions are optimized to minimize off-target hybridization and maximize target hybridization [Roy, 2011]. This optimization need for better sensitivity and will use ref [Roy, 2011] as the foundation for optimization. Details follow below.

Fluorescently labeled complementary DNA primers were added in excess amount (10 times higher than the expected target molarity) to the isolated miRNA sample and hybridization was performed at elevated temperature. Briefly, sample was heated up to 95° C. for 5 minutes and left at room temperature for one hour for the hybridization.

Step C: Dielectrophoretic capture of fluorescently labeled miRNA-DNA duplexes near electrodes. The miRNA mixture from step B is added to the PIAM. The DEP force is used to selectively localize and trap miRNA-DNA duplexes at hotspots. Previous experimental studies demonstrated that exposure of RNA molecules to AC electric fields and DEP does not destroy or alter their molecular functionality, so it is safe on miRNA [Nawarathna, 2009]. Mathematically DEP (FDEP) is represented as $$F_{DEP} = \frac{1}{2}\alpha \nabla(|E|^2) \quad (1)$$

where α is the polarizability of the molecule, E is the root-mean square of the electric field and $\nabla(E^2)$ is the electric field gradient [Pethig, 1997, Morgan, 1999]. The $\nabla(E^2)$ is dependent on the shape of the electrodes. For example, electrodes with sharp edges typically have very large $\nabla(E^2)$ [Nawarathna, 2009]. The peripheries of PIAMs are designed to have plasmonic nano-hotspots with sharp nanoscale features (FIG. 01F). Therefore, the vicinity of the plasmonic hotspots will have a very large $\nabla(E^2)$. The α has a sign and a numerical value [Pethig, 1997, Morgan, 1999, Nawarathna, 2009]. The sign of α can be positive or negative depending on the frequency of the electric field and molecule type (proteins, miRNA, DNA, etc.) [Pethig, 1997]. Positive indicates an attractive DEP that migrates the molecule toward the highest $\nabla(E^2)$, and negative indicates a repulsive DEP that migrates the molecule away from the highest $\nabla(E^2)$. The numerical value of α is based on the conductivity of the buffer [Pethig, 1997]. According to the theory of dielectric polarization, the hybridized miRNA-DNA duplexes will interact with electric fields in a manner similar to that of double-stranded DNA, whereas the other RNAs will behave like single-stranded DNAs [Chou, 2002, Jackson, 1999]. The frequency that generates a large positive α on miRNA-DNA duplexes and a large negative or no α or on nontarget RNAs is generated. The resulting force will selectively trap target miRNA-DNA duplexes at plasmonic hotspots. Trapping mechanism of miRNA-DNA duplexes in hotspots involve, first, bringing the molecules toward the periphery of pearls by $\nabla(E^2)$ between pearls. Second, local high $\nabla(E^2)$ generated in the hotspots pulls molecules from periphery of pearls to hotspots. The miRNA sample was added on the electrodes and AC electric field (10 Vpp and 1 MHz) was applied for about 20 minutes.

Step D: Excitation of fluorophore molecules and recoding an image. Once miRNA-DNA duplexes are in plasmonic hotspots, molecules are excited using an appropriate wavelength of light. The plasmonic effects of the hotspots will enhance fluorescence emission of the fluorophores. When fluorophores are close to the metal (gold) surface (<10 nm), fluorescence will be quenched by the surface plasmons. When miRNA-DNA duplexes are located between 10 nm and 100 nm from the metal, fluorescence emission will be enhanced via several plasmonic mechanisms. These mechanisms are induced through the local electric field generated by the excitation light and include: (a) enhancement of excitation intensity, (b) reduction of the fluorophore radiative decay rate, and (c) enhancement of fluorophore quantum yields [Lakowicz, 2001]. In this step, the attractive DEP is used to localize target miRNAs to metal electrodes and the repulsive DEP is used to move the molecules to an appropriate distance from plasmonic hotspots. Attractive and repulsive DEP are well-established concepts that are widely used in separation and concentration experiments [Nawarathna, 2009, Huang, 2002, Wang, 2000]. When molecules are located at the proper distance, a maximum fluorescence enhancement of up to one billion-fold is possible. The sample is excited with appropriate light source (Excitation: 495 nm, Emission: 519 nm) and an image recorded.

Figure 9:
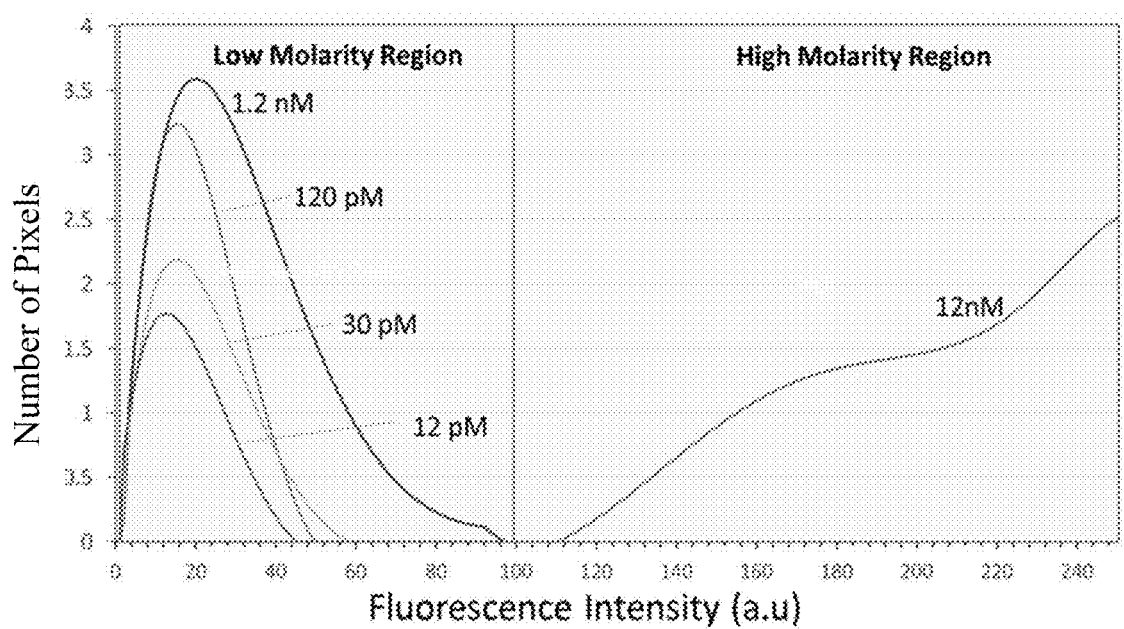

Step E: Data analysis and determine the molarity. In this step a fluorescence image of the sample is collected. The image is loaded into freely available ImageJ software and adjusted the brightness and sharpness. Finally, custom made computer program (in Matlab) is used to extract the fluorescence intensity of each pixel of the image and plotted as a histogram. The Matlab program used in the image analysis is listed below:

I=imread('image name');
R=imhist(I(:,:,1));
G=imhist(I(:,:,2));
B=imhist(I(:,:,3));
figure, plot(R,'r')

hold on, plot(G,'g')
plot(B,'b')
legend('Red channel','Green channel','Blue channel');
hold off For a sample with unknown level of miRNA, the number of pixels versus fluorescence intensity is plotted and the molarity of target miRNA molecules is calculated by comparing it with a standard curve of known molarities. FIG. 6 below shows the steps of the assay. In summary, one embodiment of the present invention is the successful integration of the PIDEs with plasmonic hotspots for the detection of biomarker molecules. The positive DEP is efficiently bringing biomarker molecules and placing them in plasmonic hotspots. A reduction of the fluorescence lifetime of the molecules that are placed in the electrodes was also measured. The observed reduction in lifetime of molecules is a direct result of the molecular interaction with enhanced electric fields in the hotspots and/or surface plasmon polaritons (SPPs). However, SPPs decay with the square of the electric field and therefore SPP effects will be limited the on smaller quantity of molecules that are near the electrode-glass interface. In contrast, molecular interactions with enhanced electric fields in hotspots do not dependent on the proximity to the electrodes and therefore it provides significant contribution to the measured reduction of fluorescence lifetime. These effects combined to contribute to the observed million-fold improvement of the current detection limit. One embodiment of the present invention demonstrates the employment of DEP in placing molecules in strategic locations so that they will be subjected to plasmonic effects (SPPs or interactions with high electric fields in the hotspots). Finally, with a few more modifications, this technology can be translated into equipment for detecting and quantifying disease related molecules in real biological samples at point-of-care settings. FIG. 9 shows fluorescence intensity f (a.u.) for miRNA-Let-7a.

Example 4: T-shaped Electrode Electric Fields

Figure 10:
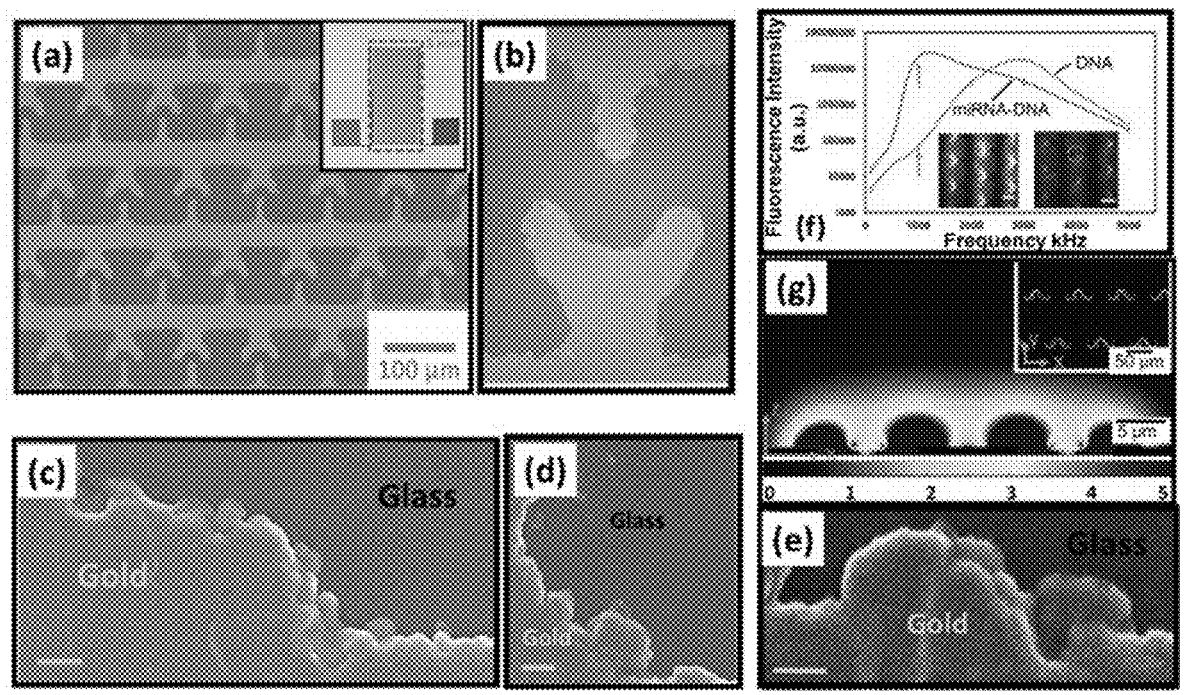
FIG. 10: Characterization of TIAMs, T-electrodes and hotspots. (a) Scanning Electron Microscope (SEM) image of the TIAM electrodes. Inset shows a picture of TIAM electrodes fabricated on a glass wafer. Rectangle with broken lines indicates the area of TIAMs electrodes. The two squares outside the TIAMs are the contact pads for establishing electrical connection. (b) SEM image of a single T-electrode. Note that the rough edges contain large number of hotspots. (c-e) SEM images of hotspots that are fabricated in the periphery of a T-electrode. Scale bars are 200 nm. Note that sizes of hotspots vary from 20-400 nm however, the majority of hotspots are about 100 nm in size (data not shown). (f) Variation of fluorescence intensity with the frequency of the applied external potential for miRNA-DNA and DNA molecules. Note that at 1 MHz miRNA-DNA can be concentrated on the hotspots without interference with probe DNA molecules. Fluorescence intensities at 1 MHz is indicated in blue arrows. Insets show the snap shots of fluorescence images (scale bars are 50 µm). Image with bright fluorescence is for miRNA-DNA duplexes and circles with broken lines indicate the areas where combination thermophoresis, diffusion and dielectrophoresis concentrate molecules. (g) Calculated electric field gradient values (in $10^{17}$ $V^2/m^3$) across a T-electrode. Electrodes are indicated in black rectangles and they are not drawn to a scale. Inset shows the variation of electric field gradient in the x-y plane (z=100 nm).

In another embodiment of the present invention, T-shaped interdigitated array of microelectrodes (TIAMs) have been developed. TIAMs have nano-scale plasmonic structures, called hotspots, in the periphery of TIAMs. FIG. 10(a) shows the TIAMs fabricated on the glass substrate. The TIAMs were fabricated using a low-resolution photolithography mask, and the photoresist film was overexposed to UV light during photolithography to produce metal structures with rough edges [Velmanickam 2017]. These rough features are the nanoscale plasmonic structures (or hotspots) utilized in the miRNA detection (FIG. 1(a-e)). Details about manufacturing hotspots can be found elsewhere [Velmanickam 2017]. Historically, an E-beam lithography technique has been used to produce structures on this scale [Altissimo 2010]. E-beam lithography is expensive and is a low-throughput nanofabrication method that costs thousands of dollars to produce a single electrode [Altissimo 2010]. Therefore, E-beam lithography is not a feasible path for producing electrodes for diagnostic applications. The one-step traditional photolithography method produces hotspots that vary from 20-400 nm (average approximately 100 nm) with excellent reproducibility. Although the sizes of the hotspots vary from TIAM electrode to electrode, no significant variation of fluorescence enhancement because of change in the nanostructures was observed.

The fluorescence intensity variation with frequency of the electric field near a single T-electrode, between let-7b miRNA hybridized to a fluorescein-labeled DNA probe and a single-stranded let-7b DNA probe was measured. This experiment was needed to identify the frequency at which miRNA-DNA molecules are selectively concentrated in T-electrodes. The frequency was varied between 100 kHz and 5 MHz, for each frequency and a fluorescence image at individual frequencies was recorded. At 1 MHz, let-7b miRNA-DNA hybridized molecules were concentrated to a greater extent (approximately 200×) in the T-electrodes with minimum contamination from complementary free DNA molecules (FIG. 10(f)). Moreover for comparison of fluorescence at 1 MHz, two fluorescence images (inset), one of the complementary DNA probe and one of the miRNA-DNA duplex (FIG. 10(f) inset) are illustrated.

The combination of thermophoresis, diffusion, and dielectrophoresis produced a selective concentration of miRNA-DNA molecules. Mathematically, dielectrophoretic force (FDEP), thermophoretic diffusion (j), diffusion velocity (v) are represented as, $$F_{DEP} = \tfrac{1}{2}\alpha \nabla(E^2) - (1), \quad \vec{j} = -D_T c \nabla T - (2),$$
$$\vec{v} = -D \nabla c - (3),$$

where $D_T$ is the thermophoretic mobility, $D$ is the diffusion coefficient, $c$ is the concentration of molecules, $\nabla T$ is the temperature gradient, $\alpha$ is the electric polarizability of the molecule, $E$ is the root-mean square of the electric field, and $\nabla(E^2)$ is the electric field gradient [Nawarathna 2009, Duhr 2006]. $\nabla(E^2)$ is dependent on the shape of the electrodes. Half-circular-T-shaped TIAM electrodes were used because this design concentrates the electric field much better than traditional interdigitated electrodes [Velmanickam 2017]. Therefore, these T-shaped electrodes produce larger electric field gradients ($10^{17}$ V$^2$/m$^3$ range) than other designs. FIG. 10(g) shows the calculated variation of the electric field gradients in x-z and x-y (inset) planes. From this calculation, it can be concluded that the peripheries of TIAMs have nanostructures with sharp nano-scale features generates electric field gradients in the range of $10^{17}$ V$^2$/m$^3$ range (FIG. 10(g)).

Figure 11:
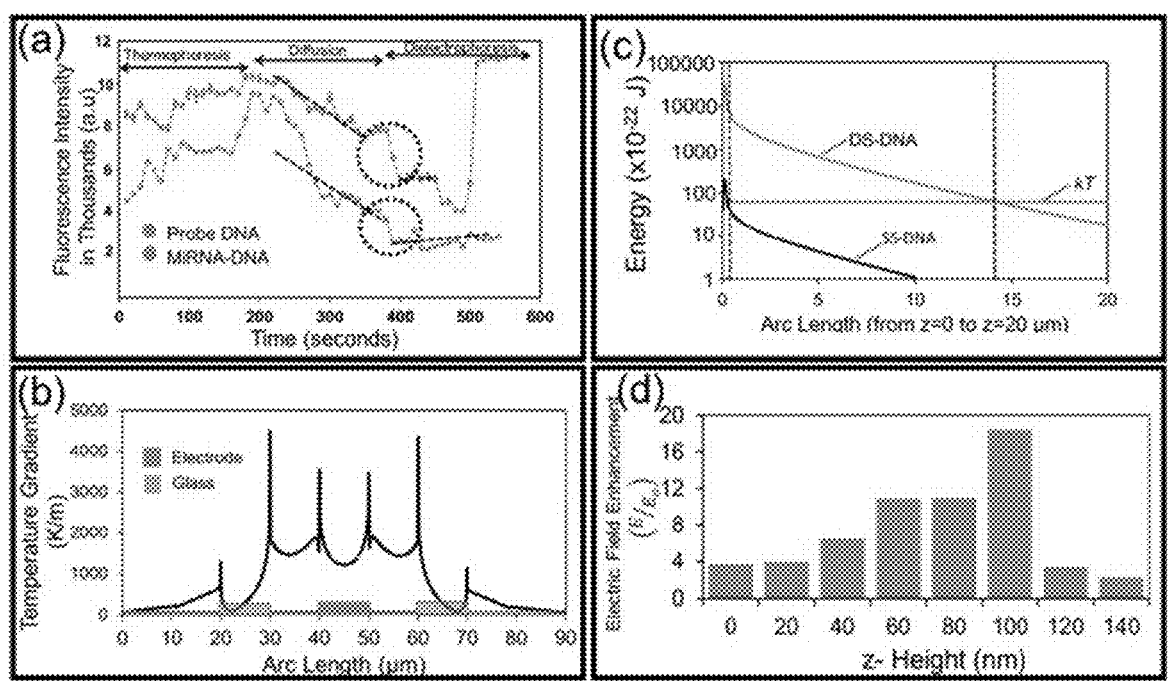
FIG. 11: Selective concentration of miRNA-DNA duplexes in hotspots and subsequently enhancing the fluorescence. (a) Variation of fluorescence intensity in a T-electrode with time for miRNA-DNA duplex and DNA probe molecules. Thermophoresis, diffusion and dielectrophoresis were produced by applying an electric potential of 10 Vpp, 1 MHz. Note that at 1 MHz, miRNA-DNA duplex molecules is selectively concentrated in T-electrodes. (b) Calculated temperature gradient values in the x-y plane of the TIAMs. According to the calculation, large temperature gradients (>1000 K/m) are produced on the edges of the T-electrodes. The smallest temperature gradients (<1000 K/m) are produced on the tops of the electrodes. (c) Variations of energies harnessed from electric fields and temperatures (at 1 MHz) by miRNA-DNA (or double stranded DNA) and DNA with the distance from TIAM electrodes. Note that electric fields or dielectrophoresis produce strong and long-range dielectrophoretic force on miRNA-DNA (or double stranded DNA) molecules extending up to about 15 µm from the electrode edges. Similarly, dielectrophoretic forces produced on the DNA probe molecules are weak and short-range extending about 1 µm from the electrodes. (d) Calculated electric field enhancement from the scattered light in the z-direction. The largest electric field enhancement was produced 100 nm from the glass surface.

To systematically study the concentration of molecules in hotspots, the variation of fluorescence with time was measured for let-7b miRNA-DNA duplexes and single-stranded let-7b DNA probe, respectively (FIG. 11(a)). A 1 MHz, 10 Vpp AC was applied potential that produces electric fields equally across all TIAMs. The magnitude of the electric field (E) produced by the AC potential is in the range of 107 V/m, and the electric field produced an energy of ($\sigma|E^2|/2$) in the TE buffer, where a is the conductivity of the buffer at 1 MHz [Marafona 2006]. This energy is partially converted to thermal energy and, as a result, the buffer solution temperature becomes slightly elevated. An approximately 7° C. increase in the buffer solution was measured (data not shown; conductivity=5 μS/cm). In parallel, a finite element modeling simulation was developed and the spatial temperature distribution and temperature gradient were calculated (FIG. 11(b)).

As the buffer heats up, evaporation is increased, taking about 8 min for the buffer to evaporate. In parallel, the temperature gradient in the TE buffer results in thermophoresis (resulting in thermal diffusion) of the molecules. According to the calculations, an average temperature gradient of ≈3000 K/m produced significant thermophoretic diffusion of the molecules (FIG. 11(b)). The various classes of molecules (single versus double stranded nucleotides) in the sample responded in a similar fashion by becoming concentrated near hotspots, during thermophoresis (0-200 s FIG. 11(a)) [Reichl 2015]. As molecules become concentrated in T-electrodes, molecular crowding occurs in the concentrated areas, resulting in an increase in the diffusion current that pushes molecules away from highly concentrated areas. As a result of diffusion, the fluorescence intensity near the T-electrodes gradually decreased (FIG. 11(a), 200-400 s). The diffusion current drives molecules to the top of the electrodes, where the thermal diffusion of molecules is relatively small. The temperature gradient distribution in the x-z plane (FIG. 11(b)) was used to confirm this observation. Note that temperature gradients have minimum values over the electrodes.

After concentration of molecules using thermophoresis, the differential effects of dielectrophoretic force on single and double stranded nucleic acids was investigated. The time point when the dielectrophoresis is activated was determined by observing the change of slope of the fluorescence versus time curve (FIG. 11(a), 300-400 seconds). The data demonstrates that at 1 MHz the increase of fluorescence of miRNA-DNA duplexes was significantly greater than the dielectrophoretic force experienced by the single-stranded DNA probe. As stated above, the single-stranded DNA probes move to the top of the electrodes by diffusion and is not detected by an inverted fluorescent microscope (see FIG. 11(b)).

The strength of dielectrophoretic force varies with the distance from the T-electrode. the variation of electric energy absorbed from AC electric fields by let-7b miRNA-DNA duplexes and single-stranded let-7b DNA probes that were located along a contour in the z-direction were calculated and compared to the thermal energy of the molecules (FIG. 11(c)) [Nawarathna 2009]. According to the calculation, electric energy of miRNA-DNA molecules was significantly larger than the thermal energy of the same molecules within about 10-15 µm from the electrodes. In comparison, single-stranded DNA molecules failed to be concentrated at the same distance from the electrode (10 µm). Therefore, at 1 MHz, dielectrophoresis is not efficient for concentrating DNA molecules. Collectively, the above mechanism can be utilized to selectively distinguish target miRNA-DNA duplexes from free single-stranded DNA probes. The interplay between thermophoresis and diffusion in concentrating molecules is critical to the success of the miRNA detection. In fact, diffusion is the mechanism that is used to exclude fluorophore-labeled DNA molecules from being detected.

It was further examined how hotspots scattered the excitation light and produced an enhanced electric field. Another calculation was developed to determine the enhancement of the electric field along a contour in the z-direction, where z=0 represents the glass substrate (FIG. 11(d)). The square of the electric field enhancement is the expected fluorescence enhancement [Lakowicz 2001]. According to the calculation, a maximum enhancement of about 202-fold is expected from the miRNA-DNA duplexes at the top edge of the electrodes (z=100 nm). The details of this calculation are included in the materials and methods section.

The ability of dielectrophoresis to place fluorophores in the region of a large electric field from the scattered incident light was then tested. Fluorescein (excitation: 490 nm, emission: 520 nm)-labeled miRNA-DNA duplexes were used in an embodiment of the present invention. Fluorescein was selected because it has a high quantum yield (approximately 0.9) and therefore it is a stable fluorophore [Lakowicz 2001]. To produce dielectrophoresis, an AC electric field of 10 Vpp with 1 MHz was applied to the fluorescein-labeled miRNA-DNA duplexes, thereby concentrating the molecules to the hotspots, then recording an image. As a negative control experiment, single-stranded complementary DNA molecules (without miRNA) were concentrated with 10 Vpp and 1 MHz AC potential. Exclusively using the miRNA-DNA duplexes, the fluorescence of each pixel within each image was extracted and plotted as histograms (number of pixels versus fluorescence intensity, FIG. 12(a)). By comparing the two histograms, two distinct regions were observed, labeled Region 1 and Region 2. Region 1 represented a low fluorescence area where dielectrophoresis did not concentrate duplex molecules into hotspots. In contrast, Region 2 represented a high fluorescence area where dielectrophoresis actively concentrated duplex molecules into hotspots. Within Region 2, there were two distinct fluorescence distributions, which is labeled population 1 and 2. The broadly distributed population 1 is from enhancement via a larger collection of hotspots caused by a comparatively small electric field produced by the scattering of light. The narrowly distributed population 2 was from enhancement via light scattering with small hotspots due to the production of a large electric field. Therefore, regardless of the nature of scattering, this demonstrates that dielectrophoresis can be used to concentrate molecules in regions that have a large electric field generated by the scattered light.

Materials and Methods

Variation of fluorescence with frequency for SS-DNA and DS-DNA (FIG. 10(f))—Frequencies were varied to distinguish target miRNA-DNA duplexes from single stranded DNA probes. Fluorescein labeled single stranded DNA probes and miRNA-DNA duplexes at 100 nM in 10 µl were pipetted on the top of the TIAM electrode array and fluorescent measurements were recorded while varying the frequency form 0.1, 0.5, 1, 2, 3, 4 and 5 MHz with 10 Vp-p. Histogram graphs of the fluorescent intensity for each sample was plotted and the total enhanced fluorescence intensity was calculated by analyzing the intensities from 101 to 255 with background intensities below 100 eliminated. Total enhanced intensities were plotted with frequencies. Insets represent fluorescence intensity comparisons between miRNA-DNA duplexes and single stranded DNAs at 1 MHz.

Calculation of electric field gradient (FIG. 10(g))—The electric field gradient ($|\nabla E^2|$) produced by the TIAM electrode array was calculated using AC/DC module frequency domain studies in COMSOL Multiphysics® software. The TIAM electrode array was drawn to scale in AutoCAD software and imported to the COMSOL software. Then the 0.01× TE buffer (5 µS/cm) was added over the TIAM electrode array. The geometry was meshed using swept mesh technique (extremely fine mesh; maximum element size—0.1 µm, minimum element size 0.001 µm). Finally 10 Vp-p voltage, 1 MHz frequency sinusoidal signal was applied to the electrode and the simulation was performed. From the simulation results the $|\nabla E^2|$ was calculated. The main figure shows the $|\nabla E^2|$ of the TIAM electrode array in X-Z plane. Inset shows the $|\nabla E^2|$ of the TIAM electrode array in X-Y plane (@ Z=50 nm).

Variation of fluorescence with time (FIG. 11(a))—Fluorescein (excitation −492 nm, emission −515 nm) labeled complementary human-miR-let-7b and a hybridized human-miR-let-7b miRNA complementary DNA duplex was purchased from Midland Certified Reagent Company INC. (Midland, Tex., USA). Single and hybridized samples were prepared in 0.01× TE buffer (5 µS/cm) at 1 µM and fluorescent measurements were performed separately as indicated for each sample using a XDY-1 Inverted Fluorescence Microscope (Wuzhou, Guangxi, China). Samples were pipetted over the TIAM electrode array and a 10 Vp-p, 1 MHz frequency sinusoidal signal was applied (t=0 second) using Tektronix AFG 3021B Single channel function generator (Beaverton, Oreg., USA). Fluorescent images were taken by a Motic 10 MP camera every 10 seconds until the sample was dry (approximately 10 minutes). Fluorescent images of TIAM electrode arrays were analyzed with Imagej software and the total fluorescence intensity (TFI) for each sample was calculated every 10 seconds. TFI was determined by multiplying the intensity (0-255) by corresponding pixel count in the histogram and taking the sum of the multiplication. Finally the total intensity was plotted with time for each single stranded DNA and miRNA-DNA duplex separately.

Calculation of temperature gradients (FIG. 11(b))—The temperature and temperature gradients ($\nabla T$) were calculated by using joule heating module in COMSOL Multiphysics® software (5.2a, Burlington, Mass.). First, the TIAM electrode array was drawn to scale using AutoCAD software and imported into the COMSOL software. Second, 0.01× TE buffer (5 μS/cm) was added over the TIAM electrode array. Third, an electric potential of 10 Vp-p and 1 MHz sinusoidal signal was applied to the electrode and the geometry was meshed (extremely fine mesh; maximum element size-0.1 μm, minimum element size 0.001 μm) using a swept mesh technique. The initial temperature was defined as 300K and the simulation was performed by varying the time (0-10 minutes). Lastly, the temperature and $\nabla T$ were calculated from the simulation results (0-10 minutes). Inset shows the temperature distribution at 5 minutes and the figure shows the $\nabla T$.

Calculation of electric fields produced by scattered light (FIG. 11(d))—The electric field enhancement capability of the hotspots was determined by using the Wave optics module, electromagnetic waves frequency domain (EWFD) studies in COMSOL Multiphysics® software. The hotspots were drawn to scale using AutoCAD software and imported into the COMSOL software. The design was meshed using swept mesh technique (extremely finer mesh; maximum element size—0.1 nm, minimum element size 0.001 nm). Hotspots were illuminated through 500 nm wavelength and the electric field was calculated. From the simulation results, the normalized electric field enhancement was calculated at different planes of the electrode through cut-lines.

Example 5: T-Electrodes and Calculating miRNA Molarity of a Sample

First, a family of standard curves are constructed. These curves are used as a reference in calculating molarity, and they were produced by running two experiments (with and without target miRNA molecules) and calculating the fluorescence with miRNA/without miRNA for each molarity (FIG. 12(b)). For unknown molarities, fluorescence with miRNA/without miRNA was calculated and plotted with the standard curves. The molarity was then calculated based on the location of the curve or the peak of the curve. These standard curve can be utilized to detect unknown molarities of samples. Next, the data shows that the iLluminate-miRNA method was able to detect Let-7b miRNA in a quantitative and specific manner. Water and human serum solutions, which were spiked with known concentrations of Let-7b miRNA were used. Samples were divided equally after column chromatography, measured by the iLluminate-miRNA and compared to qRT-PCR measurements. It is worth noting the rapid measurement time and cost-effective nature of the iLluminate-miRNA method relative to qRT-PCR (FIG. 13(a)). Both the iLluminate-miRNA method and qRT-PCR were effective at measuring purified Let-7b miRNA (range: 0.0114 pM-12 nM) spiked into water (FIG. 13(b) and Table 1) or human serum (FIG. 13(c) and Table 2). However, comparison of the percent recoveries of spiked-in Let-7b miRNA to a 100% predicted recovery (represented as triangles and corresponding line in FIGS. 13(b and c)), clearly showed that the iLluminate-miRNA method was more accurate and precise at all spiked-in Let-7b miRNA concentrations using both water and human serum as solvents. Compared to qRT-PCR, the iLluminate-miRNA method resulted in smaller standard errors of the mean (SEM) for Let-7b miRNA concentrations (Tables 1 and 2), especially in water. To ensure specificity, FIG. 13(d) illustrates the detection of 12 nM of Let-7b miRNA, but not a randomly generated miRNA (22 mer called scrambled—scr.), for the iLluminate-miRNA technique when spiked into water (set arbitrarily to 100%) or human serum (52%), respectively. The reduction in percent recovery in serum versus water for the same Let-7b miRNA (12 nM) might not be directly due to the iLluminate-miRNA detection method per se, but rather because of a reduction in Let-7b miRNA yield during column chromatography. Lastly, the iLluminate-miRNA method was nearly 10- and 660-fold more sensitive at detecting 12 nM spiked-in Let-7b miRNA compared to qRT-PCR in water or serum (FIG. 13(e)). Table 3 summarizes the overall means, +/−SEM and p values for the two methods. These results support the conclusion that the miRNA detection technique can successfully quantitate Let-7b miRNA molecules after purification from water or biological fluids in an inexpensive, rapid, accurate, and precise manner that outperforms the current gold-standard approach of qRT-PCR.

Table 1—Summary of iLluminate-miRNA and qRT-PCR Data from Spiked-in Let-7b Experiments

| | Water | | | | | | |
|---|---|---|---|---|---|---|---|
| | iLluminate-miRNA | | | | | | |
| [Let-7b pM] | F.I.E. Means | +/− SEM | Expected | Recovery | +/− SEM | N |
| 12000.0 | 75662143.0 | 2171322.0 | 100.0 | 100* | 2.87 | 3 |
| 3000.0 | 15425028.0 | 112101.7 | 25.0 | 81.5468734 | 0.15 | 3 |
| 750.0 | 13172686.0 | 124004.0 | 6.25 | 278.558031 | 0.16 | 3 |
| 187.5 | 576083.7 | 23188.9 | 1.56 | 48.7289326 | 0.03 | 3 |
| 46.9 | 389066.3 | 4179.0 | 0.391 | 131.568953 | 0.006 | 3 |
| 11.7 | 70961.0 | 3272.0 | 0.098 | 96.1914505 | 0.004 | 3 |
| 2.9 | 14164.0 | 3356.0 | 0.024 | 77.4623251 | 0.004 | 3 |
| 0.73 | 9673.0 | 2290.0 | 0.0061 | 209.581389 | 0.003 | 3 |
| 0.18 | 1609.0 | 334.0 | 0.0015 | 139.446482 | 0.0004 | 3 |
| 0.046 | 638.0 | 78.0 | 0.00038 | 220.931585 | 0.0001 | 3 |

-continued

| | | | Water | | | |
|---|---|---|---|---|---|---|
| 0.011 | 328.0 | 35.0 | 0.00010 | 456.322203 | 0.00005 | 3 |
| 0.000 | 0.0 | 0.0 | 0.00000 | 0 | 0 | 3 |

| | | | qRT-PCR | | | |
|---|---|---|---|---|---|---|
| [Let-7b pM] | Ct Means | +/− SEM | Expected | Recovery | +/− SEM | N |
| 12000.0 | 10.40 | 0.29 | 100 | 100* | 43.31 | 3 |
| 3000.0 | 13.69 | 0.15 | 25 | 10.24 | 59.05 | 3 |
| 750.0 | 16.47 | 0.19 | 8.25 | 1.49 | 29.22 | 3 |
| 187.5 | 19.95 | 0.59 | 1.56 | 0.13 | 88.62 | 4 |
| 46.9 | 23.32 | 0.43 | 0.391 | 1.29E−02 | 78.11 | 4 |
| 11.7 | 26.12 | 0.99 | 0.098 | 1.85E−03 | 167.70 | 4 |
| 2.9 | 28.76 | 0.77 | 0.024 | 2.98E−04 | 139.73 | 4 |
| 0.73 | 30.22 | 0.74 | 0.0061 | 1.08E−04 | 107.14 | 3 |
| 0.18 | 33.71 | 1.14 | 0.0015 | 9.62E−06 | 186.21 | 3 |
| 0.046 | 36.47 | 1.04 | 0.00038 | 1.42E−06 | 150.00 | 3 |
| 0.011 | 38.75 | 1.17 | 0.00010 | 2.93E−07 | 186.21 | 3 |
| 0.000 | 40.10 | 0.00 | 0 | 1.15E−07 | 134.69 | 3 |

*Arbitrarily set to 100%

TABLE 2

Summary of iLluminate-miRNA and qRT-PCR data from spiked-in Let-7b experiments.
Serum

| | | | iLluminate-miRNA | | | |
|---|---|---|---|---|---|---|
| [Let-7b pM] | F.I.E. Means | +/− SEM | Expected | Recovery | +/− SEM | N |
| 12000.0 | 40012795.0 | 954924.4 | 100.0 | 52.88$^\alpha$ | 2.39 | 3 |
| 120.0 | 5955.3 | 514.7 | 1.000 | 0.0079 | 0.09 | 3 |
| 60.0 | 3027.0 | 744.0 | 0.500 | 0.004 | 0.12 | 3 |
| 30.0 | 1011.7 | 277.2 | 0.250 | 0.001 | 0.07 | 3 |
| 12.0 | 588.3 | 131.1 | 0.1000 | 0.0008 | 0.02 | 3 |
| 1.2 | 132.0 | 20.0 | 0.0100 | 0.0002 | 0.002 | 3 |
| 0.0 | 13.3 | 3.8 | 0.0000 | 0.00 | 0.00 | 3 |

| | | | qRT-PCR | | | |
|---|---|---|---|---|---|---|
| [Let-7b pM] | Ct Means | +/− SEM | Expected | Recovery | +/− SEM | N |
| 12000.0 | 36.95 | 1.60 | 100.0 | 1.02E−06 | 53.96605 | 3 |
| 120.0 | 38.03 | 2.60 | 1.000 | 4.82E−09 | 29.45412 | 4 |
| 60.0 | 35.98 | 2.28 | 0.500 | 9.97E−09 | 5.806601 | 3 |
| 30.0 | 36.98 | 1.99 | 0.250 | 2.49E−09 | 1.161297 | 3 |
| 12.0 | 35.87 | 0.76 | 0.100 | 2.15E−09 | 0.086068 | 3 |
| 1.2 | 36.06 | 2.20 | 0.010 | 1.89E−10 | 0.085388 | 4 |
| 0.0 | 37.42 | 2.30 | 0.000 | 0.00E+00 | 0.023027 | 4 |

$^\alpha$ and $\beta$ - Compared to % recovery from 12 pM let-7b in water

TABLE 3

Comparison to predicted 100% recovery.

| Procedure | % recovery mean | P value | Significance |
|---|---|---|---|
| | Water | | |
| qRT-PCR | 15.45 | 0.2687 | ns |
| iLluminate-miRNA | 154.3 | 0.0001 | **** |
| | Serum | | |
| qRT-PCR | 0.01052 | 0.0001 | **** |
| iLluminate-miRNA | 8.218 | 0.0001 | **** |

P values calculated by One-Way ANOVA

Figure 12:
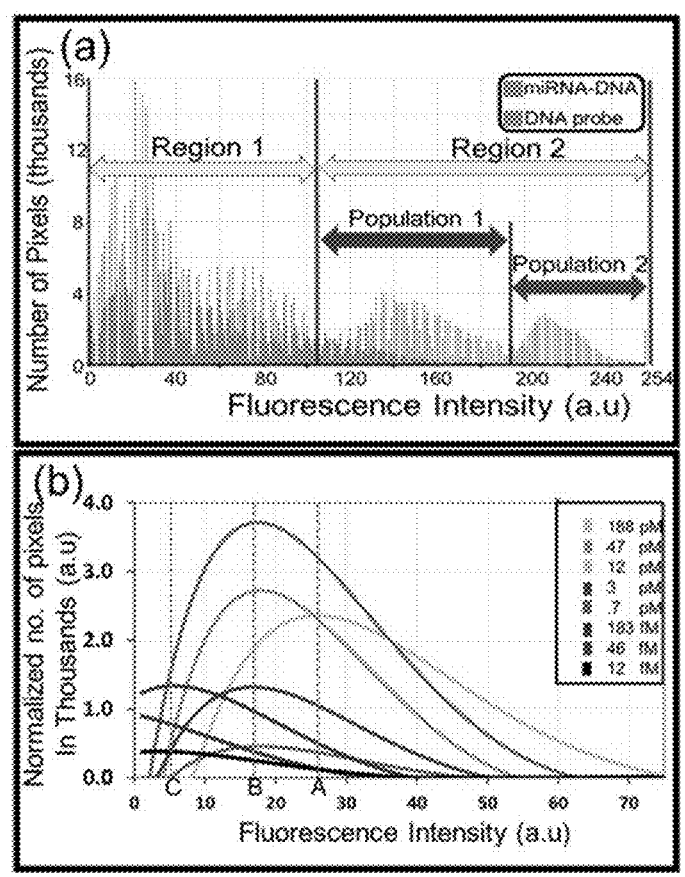
FIG. 12: Fluorescence enhancement of miRNA-DNA duplex molecules and standard curves for miRNA quantification. (a) Comparison of fluorescence from miRNA-DNA and DNA probe molecules. These molecules were concentrated using an electric potential of 10 Vpp at 1 MHz. (b) Fitted curves for the histograms of fluorescence of miRNA-DNA duplex molecules. The location of peak is dependent on the molarity of miRNA-DNA duplex molecules. For example vertical (broken line) line A corresponds to higher molarities >100 pM, line B corresponding to 1-100 pM and line C corresponds to <1 pM. These curves are used as standard curves for calculating the molarity of an unknown sample. These curves were generated from spike-in miRNA in water experiments.
Figure 13:
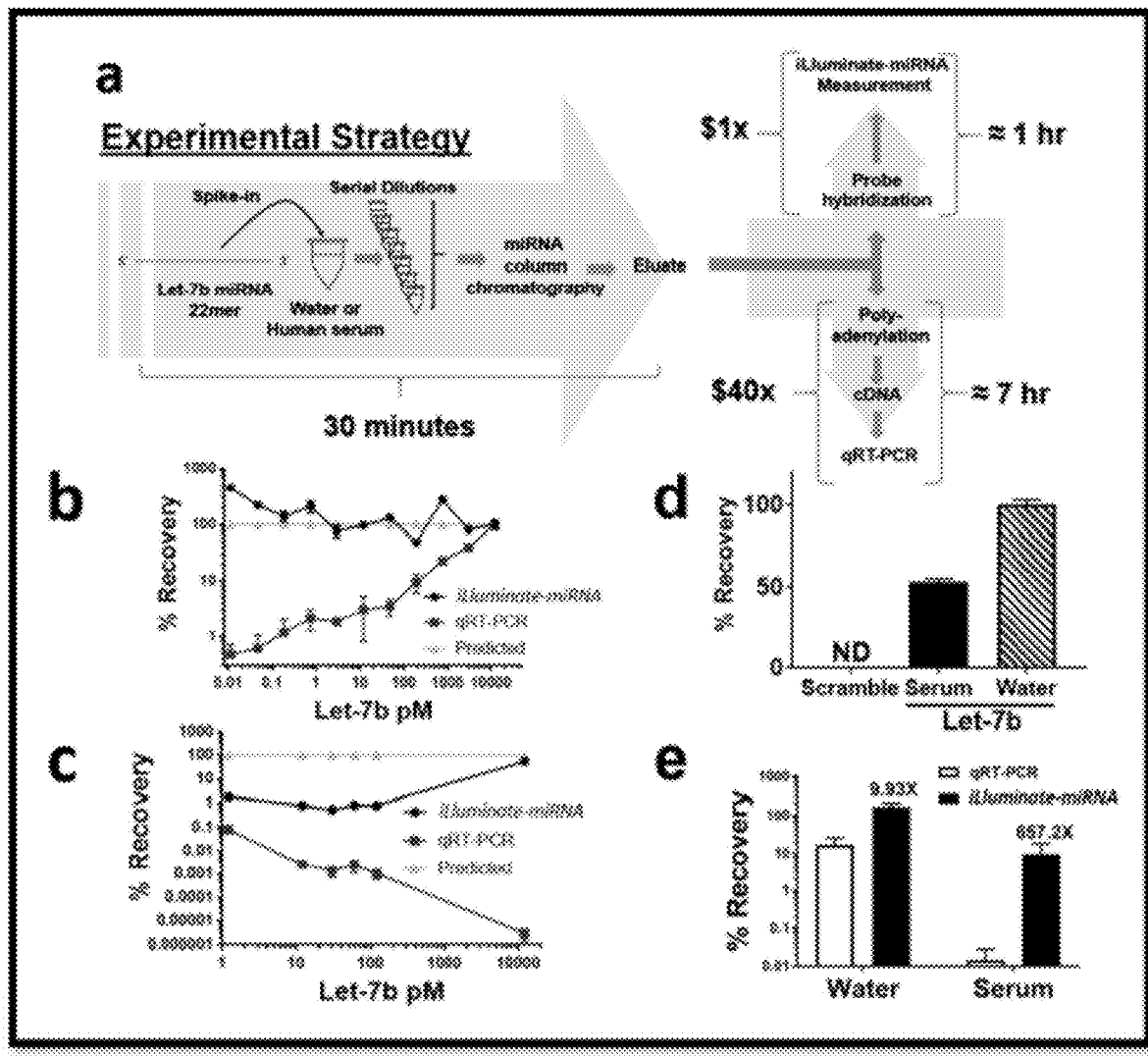
FIG. 13: Superior percent recovery of spiked-in human miRNA Let-7b by iLluminate-miRNA, as described further herein, versus qRT-PCR. (a) Experimental strategy for miRNA Let-7b spiked-in measurements. (b-c) iLluminate-miRNA versus qRT-PCR comparison for miRNA Let-7b measurement. Detection of spiked-in miRNA Let-7b in nuclease-free water, (b) or human serum (c) purified by column chromatography and measured by iLluminate-miRNA versus qRT-PCR from 3-4 independent experiments (Materials and Methods). Data is presented as line graphs with means of % recovery +/− SEM, and set arbitrarily to 100% based on the highest Let-7b concentration spiked into water (12 nM). All subsequent calculations were based on this maximum % recovery value. (d) Scrambled miRNA (12 nM) or miRNA Let-7b (12 nM) were spiked into water or human serum. Samples were subsequently purified by column chromatography and measured by iLluminate-miRNA or qRT-PCR. Data is presented as a bar graph with % recovery means +/− SEM from 3 independent experiments. The abbreviation of "ND" stands for "not detected." (e) Direct relative comparisons of % recovery calculations at 12 nM are presented in a bar graph +/− SEM from 3-4 independent experiments. The fold-difference in % recovery value for iLluminate-miRNA versus qRT-PCR is placed above the appropriate bar for both water and human serum solvents.

Generation of standard curves (FIG. 12(b))—The standard curves were determined by calculating the signal (miRNA-DNA duplexes) to noise (single stranded DNA probe) ratio. To determine the signal to noise ratio, the histogram for the miRNA-DNA duplexes were divided by the corresponding background values. The quotients were fitted into a curve using MATLAb software curve fitting tool with the polynomial curve fitting command. Data is presented as a line graph.

Measurement of let-7b by iLluminate-miRNA (FIG. 13b-e)—First, isolated human-miR-let-7b molecules were hybridized using 10 times the molar concentration of the fluorescence labelled complementary DNA probe. miRNA-DNA duplexes were hybridized by heating to 95° C. for 5 minutes and cooled at room temperature for one hour. Samples were pipetted over the TIAM electrode array and 10 Vp-p voltage 1 MHz frequency sinusoidal signal was applied. When samples dried, fluorescent images were taken and EFI was calculated. The EFI was calculated by eliminating the background intensity. The background intensity was determined by repeating the experiments with the same concentration of single stranded DNA probe and the histogram was plotted from the recorded images. From the histogram, an intensity point was determined where the pixel value was zero. Then the total EFI due to the miRNA-DNA duplex was calculated by analyzing the intensity above the determined background zero intensity value. The corresponding total EFI were calculated similarly for each concentration.

Measurement of let-7b by qRT-PCR (FIG. 13b-e)—Water or human serum were used as solvents to spike-in a known concentration of miRNA Let-7b by serial dilutions. Diluted samples were purified by using the miRNA isolation kit (SNC50 2017 Sigma-Aldrich, St. Louis, Mo., USA.) followed by qRT-PCR (600583 2017 Agilent, Santa Clara, Calif., USA) as described by the manufacturer.

Calculations for Percent (%) Recovery (Tables 1-3)—Maximum fluorescent signals from iLluminate-miRNA and qRT-PCR for 12 nM of spiked-in human-miRNA-let-7b in water was arbitrarily set to 100%, respectively. For iLluminate-miRNA, % recoveries from water or serum were calculated by taking the ratio of EFI from each diluted sample (numerator) over the EFI for 12 nM from water (denominator) and normalized by multiplying with the dilution factor (Table 1). Therefore, the maximum % recovery in human serum was 52.88% (Table 2). For qRT-PCR, Ct values for each diluted sample were subtracted from the lowest Ct value detected in water or serum ($\Delta$Ct). Fold-differences for each diluted sample were calculated by using: 2−($\Delta$Ct), and % recoveries were calculated in an identical manner as the iLluminate-miRNA (Table 1 and 2). Briefly, fold-differences for each diluted sample (numerator) were divided by its maximum at 12 nM in water (denominator) and normalized by multiplying by the dilution factor.

This iLluminate-miRNA detection methodology encompasses the following steps: 1. miRNA isolation from serum by column chromatography and suspension in a low conductivity Tris EDTA (TE) buffer (approximately 5 minutes), 2. hybridization of target miRNAs with a complementary DNA probe tagged with a fluorophore to produce miRNA-DNA duplexes of target miRNA molecules (approximately 5 minutes), and 3. the transfer of the sample (miRNA-DNA duplexes, free miRNA, and fluorophore-labeled DNA) to TIAMs for concentration, fluorescence enhancement, and molarity calculation (approximately 8-10 minutes). All of these steps may be integrated into a single disposable diagnostic platform to allow for high-throughput miRNA detection with an estimated 20 min completion time at point of care facilities. The manufacturing cost for this disposable device, including the TIAM array and reagents will be approximately $60.

The iLluminate-miRNA detection platform is further suitable to measure miRNA cancer biomarkers (miR-642b, miR-885-5p, and miR-22) cancer patient serum as reported by Ganepola et al. [Ganepola 2014]. These authors also identified a suitable internal miRNA control (miR-3196), which did not fluctuate between patients [Ganepola 2014].

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

Altissimo, M., 2010. E-beam lithography for micro-/nano-fabrication. Biomicrofluidics, 4(2), p. 026503.

Anderson, Leigh. "Candidate-based proteomics in the search for biomarkers of cardiovascular disease." The Journal of physiology 563.1 (2005): 23-60.

Anderson, N. Leigh, and Norman G. Anderson. "The human plasma proteome history, character, and diagnostic prospects." Molecular & cellular proteomics 1.11 (2002): 845-867.

Asbury, C. L., Diercks, A. H. and Van Den Engh, G., 2002. Trapping of DNA by dielectrophoresis. Electrophoresis, 23(16), pp. 2658-2666.

Barik, Avijit, et al. Dielectrophoresis-enhanced plasmonic sensing with gold nanohole arrays. Nano letters. 2014, 14(4), 2006-2012.

Basuray, S. and Chang, H. C., Induced dipoles and dielectrophoresis of nanocolloids in electrolytes. Physical Review E, 2007, 75(6), 060501.

Beger, H. G., Rau, B., Gansauge, F., Poch, B., & Link, K. H. (2003). Treatment of pancreatic cancer: challenge of the facts. World journal of surgery, 27(10), 1075-1084.

Bettazzi, Francesca, et al. "Electrochemical detection of miRNA-222 by use of a magnetic bead-based bioassay." Analytical and bioanalytical chemistry 405.2-3 (2013): 1025-1034.

Brismar, H., Trepte, O. and Ulfhake, B. Spectra and fluorescence lifetimes of lissamine rhodamine, tetramethylrhodamine isothiocyanate, texas red, and cyanine 3.18 fluorophores: influences of some environmental factors recorded with a confocal laser scanning microscope. Journal of Histochemistry & Cytochemistry. 1995, 43(7), 699-707.

Čemažar, J., Douglas, T. A., Schmelz, E. M. and Davalos, R. V. Enhanced contactless dielectrophoresis enrichment and isolation platform via cell-scale microstructures. Biomicrofluidics, 2016 10(1), 014109.

Chaurey, V., Rohani, A., Su, Y. H., Liao, K. T., Chou, C. F. and Swami, N. S., Scaling down constriction-based (electrodeless) dielectrophoresis devices for trapping nanoscale bioparticles in physiological media of high-conductivity. Electrophoresis, 2013, 34(7), pp. 1097-1104.

Chen, Caifu, et al. "Real-time quantification of microRNAs by stem-loop RT-PCR." Nucleic acids research 33.20 (2005): e179-e179.

Chen, X., Ba, Y., Ma, L., Cai, X., Yin, Y., Wang, K., Guo, J., Zhang, Y., Chen, J., Guo, X. and Li, Q., 2008. Characterization of microRNAs in serum: a novel class of biomarkers for diagnosis of cancer and other diseases. Cell research, 18(10), pp. 997-1006.

Cheng, I. F., Senapati, S., Cheng, X., Basuray, S., Chang, H. C. and Chang, H. C., A rapid field-use assay for mismatch number and location of hybridized DNAs. Lab on a Chip, 2010, 10(7), pp. 828-831.

Chou, C. F., Tegenfeldt, J. O., Bakajin, O., Chan, S. S., Cox, E. C., Darnton, N., Duke, T. and Austin, R. H., 2002. Electrodeless dielectrophoresis of single- and double-stranded DNA. Biophysical Journal, 83(4), pp. 2170-2179.

Cissell, Kyle A., and Sapna K. Deo. "Trends in microRNA detection." Analytical and bioanalytical chemistry 394.4 (2009): 1109-1116.

Clarke, R. W., White, S. S., Zhou, D., Ying, L. and Klenerman, D., Trapping of proteins under physiological conditions in a nanopipette. Angewandte Chemie International Edition, 2005, 44(24), 3747-3750.

Cuervo, A., Dans, P. D., Carrascosa, J. L., Orozco, M., Gomila, G. and Fumagalli, L. Direct measurement of the dielectric polarization properties of DNA. Proceedings of the National Academy of Sciences, 2014, 111(35), E3624-E3630.

Duhr, S. and Braun, D., 2006. Optothermal molecule trapping by opposing fluid flow with thermophoretic drift. Physical review letters, 97(3), p. 038103.

Dutta Choudhury, S., Badugu, R., Ray, K. and Lakowicz, J. R. Silver-gold nanocomposite substrates for metal-enhanced fluorescence: Ensemble and single-molecule spectroscopic studies. *The Journal of Physical Chemistry C.* 2012, 116(8), 5042-5048.

Eguia, Vasco, Tamas Adam Gonda, and Muhammad Wasif Saif. "Early detection of pancreatic cancer." JOP. Journal of the Pancreas 13.2 (2012): 131-134.

Ermolina, I. and Morgan, H., The electrokinetic properties of latex particles: comparison of electrophoresis and dielectrophoresis. *Journal of colloid and interface science,* 2005, 285(1), pp. 419-428.

Ezzati, Majid, et al. "Selected major risk factors and global and regional burden of disease." The Lancet 360.9343 (2002): 1347-1360.

Frebourg, T., Bercoff, E., Manchon, N., Senant, J., Basuyau, J. P., Breton, P., & Boureille, J. (1988). The evaluation of CA 19-9 antigen level in the early detection of pancreatic cancer. Cancer, 62(11), 2287-2550.

Friedländer, Marc R., et al. "Discovering microRNAs from deep sequencing data using miRDeep." Nature biotechnology 26.4 (2008).

Fu, C. C., Ossato, G., Long, M., Digman, M. A., Gopinathan, A., Lee, L. P., Gratton, E. and Khine, M. Bimetallic nanopetals for thousand-fold fluorescence enhancements. *Applied Physics Letters.* 2010, 97(20), 203101.

Ganepola, G. A., Rutledge, J. R., Suman, P., Yiengpruksawan, A. and Chang, D. H., 2014. Novel blood-based microRNA biomarker panel for early diagnosis of pancreatic cancer. World J Gastrointest Oncol, 6(1), pp. 22-33.

Gascoyne, P. R. and Vykoukal, J., 2002. Particle separation by dielectrophoresis. Electrophoresis, 23(13), p. 1973.

Geddes, C. D. and Lakowicz, J. R. Editorial: metal-enhanced fluorescence. *Journal of Fluorescence.* 12(2), 2002, 12, 121-129.

Goonetilleke, K. S., & Siriwardena, A. K. (2007). Systematic review of carbohydrate antigen (CA 19-9) as a biochemical marker in the diagnosis of pancreatic cancer. European Journal of Surgical Oncology (EJSO), 33(3), 266-270.

Gupta, V., Jafferji, I., Garza, M., Melnikova, V. O., Hasegawa, D. K., Pethig, R. and Davis, D. W. ApoStream™, a new dielectrophoretic device for antibody independent isolation and recovery of viable cancer cells from blood. *Biomicrofluidics,* 2012, 6(2), 024133.

Habbe, Nils, et al. "MicroRNA miR-155 is a biomarker of early pancreatic neoplasia." Cancer biology & therapy 8.4 (2009): 340-346.

Hingorani, Sunil R., et al. "Preinvasive and invasive ductal pancreatic cancer and its early detection in the mouse." Cancer cell 4.6 (2003): 437-450.

Huang, Y., Joo, S., Duhon, M., Heller, M., Wallace, B. and Xu, X., 2002. Dielectrophoretic cell separation and gene expression profiling on microelectronic chip arrays. Analytical chemistry, 74(14), pp. 3362-3371.

Huang, Zhaohui, et al. "Plasma microRNAs are promising novel biomarkers for early detection of colorectal cancer." International journal of cancer 127.1 (2010): 118-126.

Hughes, M. P., Morgan, H. and Flynn, M. F., The dielectrophoretic behavior of submicron latex spheres: Influence of surface conductance. *Journal of colloid and interface science,* 220(2), 1999, 454-457.

Iandolo, B., Antosiewicz, T. J., Hellman, A., & Zorić, I. On the mechanism for nanoplasmonic enhancement of photon to electron conversion in nanoparticle sensitized hematite films. *Physical Chemistry Chemical Physics.* 2013, 15(14), 4947-4954.

Jackson, J. D., 1999. Classical electromagnetics. J. Wiley & Sons, Inc., Singapore, pp. 330-335.

Jolley, M. E., Wang, C. H. J., Ekenberg, S. J., Zuelke, M. S. and Kelso, D. M. Particle concentration fluorescence immunoassay (PCFIA): a new, rapid immunoassay technique with high sensitivity. *Journal of immunological methods.* 1984, 67(1), 21-35.

Kawabata, T. and Washizu, M., 2001. Dielectrophoretic detection of molecular bindings. IEEE Transactions on Industry Applications, 37(6), pp. 1625-1633.

Kim, Dongwoo, Weston L. Daniel, and Chad A. Mirkin. Microarray-based multiplexed scanometric immunoassay for protein cancer markers using gold nanoparticle probes. *Analytical chemistry.* 2009, 81(21), 9183-9187.

Kim, S. K., Hesketh, P. J., Li, C., Thomas, J. H., Halsall, H. B. and Heineman, W. R. Fabrication of comb interdigitated electrodes array (IDA) for a microbead-based electrochemical assay system. *Biosensors and Bioelectronics.* 2004, 20(4), 887-894.

Kosaka, N., Iguchi, H. and Ochiya, T., 2010. Circulating microRNA in body fluid: a new potential biomarker for cancer diagnosis and prognosis. Cancer science, 101(10), pp. 2087-2092.

Lakowicz, J. R., Radiative decay engineering: biophysical and biomedical applications. *Analytical biochemistry.* 2001, 298(1), 1-24.

Lee, E. J., Gusev, Y., Jiang, J., Nuovo, G. J., Lerner, M. R., Frankel, W. L., Morgan, D. L., Postier, R. G., Brackett, D. J. and Schmittgen, T. D., 2007. Expression profiling identifies microRNA signature in pancreatic cancer. International journal of cancer, 120(5), pp. 1046-1054.

Li, H. and Bashir, R. Dielectrophoretic separation and manipulation of live and heat-treated cells of Listeria on microfabricated devices with interdigitated electrodes. *Sensors and Actuators B: Chemical.* 2002, 86(2), 215-221.

Li, Haibo, and Rashid Bashir. Dielectrophoretic separation and manipulation of live and heat-treated cells of Listeria on microfabricated devices with interdigitated electrodes. *Sensors and Actuators B: Chemical.* 2002, 86(2), 215-221.

Liao, K. T., Tsegaye, M., Chaurey, V., Chou, C. F. and Swami, N. S., Nano-constriction device for rapid protein preconcentration in physiological media through a balance of electrokinetic forces. *Electrophoresis,* 2012, 33(13), pp. 1958-1966.

Lisi, P. J., Huang, C. W., Huffman, R. A. and Teipel, J. W. A fluorescence immunoassay for soluble antigens employing flow cytometric detection. *Clinica Chimica Acta.* 1982, 120(2), 171-179. Epstein, J. R. and Walt, D. R. Fluorescence-based fibre optic arrays: a universal platform for sensing. *Chemical Society Reviews.* 2003, 32(4), 203-214.

Liu, R., Chen, X., Du, Y., Yao, W., Shen, L., Wang, C., Hu, Z., Zhuang, R., Ning, G., Zhang, C. and Yuan, Y., 2012. Serum microRNA expression profile as a biomarker in the diagnosis and prognosis of pancreatic cancer. Clinical chemistry, 58(3), pp. 610-618.

Lodes, Michael J., et al. "Detection of cancer with serum miRNAs on an oligonucleotide microarray." PloS one 4.7 (2009): e6229

Lofton-Day, C., Model, F., DeVos, T., Tetzner, R., Distler, J., Schuster, M., Song, X., Lesche, R., Liebenberg, V., Ebert, M. and Molnar, B., 2008. DNA methylation biomarkers for blood-based colorectal cancer screening. Clinical chemistry, 54(2), pp. 414-423.

Lopez, Alan D., et al. "Global and regional burden of disease and risk factors, 2001: systematic analysis of population health data." The Lancet 367.9524 (2006): 1747-1757.

Lu, Guowei, et al. Plasmonic-enhanced molecular fluorescence within isolated bowtie nano-apertures. Acs Nano. 2012, 6(2), 1438-1448.

Lu, Y., Liu, T., Lamanda, A. C., Sin, M. L., Gau, V., Liao, J. C. and Wong, P. K., AC electrokinetics of physiological fluids for biomedical applications, Journal of laboratory automation, 2015, 20(6), pp. 611-620.

Lusi, E. A., et al. "Innovative electrochemical approach for an early detection of microRNAs." Analytical chemistry 81.7 (2009): 2819-2822

Maier, Stefan A., and Harry A. Atwater. Plasmonics: Localization and guiding of electromagnetic energy in metal/dielectric structures. Journal of Applied Physics. 2005, 98(1), 011101.

Mendes, P. M., Jacke, S., Critchley, K., Plaza, J., Chen, Y., Nikitin, K., Palmer, R. E., Preece, J. A., Evans, S. D. and Fitzmaurice, D., Gold nanoparticle patterning of silicon wafers using chemical e-beam lithography. Langmuir, 2004, 20(9), 3766-3768.

Marafona, J. and Chousal, J. A. G., 2006. A finite element model of EDM based on the Joule effect. International Journal of Machine Tools and Manufacture, 46(6), pp. 595-602.

Mitchell, P. S., Parkin, R. K., Kroh, E. M., Fritz, B. R., Wyman, S. K., Pogosova-Agadjanyan, E. L., Peterson, A., Noteboom, J., O'Briant, K. C., Allen, A. and Lin, D. W., 2008. Circulating microRNAs as stable blood-based markers for cancer detection. Proceedings of the National Academy of Sciences, 105(30), pp. 10513-10518.

Miura, F., Takada, T., Amano, H., Yoshida, M., Furui, S., & Takeshita, K. (2006). Diagnosis of pancreatic cancer. HPB, 8(5), 337-342.

Morgan, H., Hughes, M. P., & Green, N. G. (1999). Separation of submicron bioparticles by dielectrophoresis. Biophysical journal, 77(1), 516-525.

Mulvihill, M. J., Ling, X. Y., Henzie, J., & Yang, P. Anisotropic etching of silver nanoparticles for plasmonic structures capable of single-particle SERS. Journal of the American Chemical Society. 2009, 132(1), 268-274.

Murray, Christopher J L, Alan D. Lopez, and World Health Organization. "The global burden of disease: a comprehensive assessment of mortality and disability from diseases, injuries, and risk factors in 1990 and projected to 2020: summary." (1996).

Nawarathna, D., T. Turan, and H. Kumar Wickramasinghe. "Selective probing of mRNA expression levels within a living cell." Applied physics letters 95.8 (2009): 083117

Nakano, A. and Ros, A., Protein dielectrophoresis: advances, challenges, and applications. Electrophoresis, 2013, 34(7), 1085-1096.

Nakano, A., Luo, J. and Ros, A., Temporal and spatial temperature measurement in insulator-based dielectrophoretic devices. Analytical chemistry, 2014, 86(13), pp. 6516-6524.

Nawarathna, D., Norouzi, N., McLane, J., Sharma, H., Sharac, N., Grant, T., Chen, A., Strayer, S., Ragan, R. and Khine, M. Shrink-induced sorting using integrated nanoscale magnetic traps. Applied physics letters. 2013, 102(6), 063504.

Nawarathna, D., Turan, T. and Wickramasinghe, H. K. Selective probing of mRNA expression levels within a living cell. Applied physics letters. 2009, 95(8), 083117.

Nawarathna, D., Turan, T. and Wickramasinghe, H. K., 2009. Selective probing of mRNA expression levels within a living cell. Applied physics letters, 95(8), p. 083117.

Osman, I., Bajorin, D. F., Sun, T. T., Zhong, H., Douglas, D., Scattergood, J., Zheng, R., Han, M., Marshall, K. W. and Liew, C. C., 2006. Novel blood biomarkers of human urinary bladder cancer. Clinical Cancer Research, 12(11), pp. 3374-3380.

Patterson, G. H., Knobel, S. M., Sharif, W. D., Kain, S. R. and Piston, D. W. Use of the green fluorescent protein and its mutants in quantitative fluorescence microscopy. Biophysical journal. 1997, 73(5), 2782.

Pethig, R. Review article—dielectrophoresis: status of the theory, technology, and applications. Biomicrofluidics, 2010, 4(2), p. 022811.

Pethig, R., & Markx, G. H. (1997). Applications of dielectrophoresis in biotechnology. Trends in biotechnology, 15(10), 426-432.

Pommer, M. S., Zhang, Y., Keerthi, N., Chen, D., Thomson, J. A., Meinhart, C. D. and Soh, H. T. Dielectrophoretic separation of platelets from diluted whole blood in microfluidic channels. Electrophoresis. 2008, 29(6), 1213-1218.

Reichl, M., Herzog, M., Greiss, F., Wolff, M. and Braun, D., 2015. Understanding the similarity in thermophoresis between single- and double-stranded DNA or RNA. Physical Review E, 91(6), p. 062709.

Roy, S., Soh, J. H. and Gao, Z., 2011. A microfluidic-assisted microarray for ultrasensitive detection of miRNA under an optical microscope. Lab on a Chip, 11(11), pp. 1886-1894.

Rusling, James F., et al. Measurement of biomarker proteins for point-of-care early detection and monitoring of cancer. Analyst. 2010, 135(10), 2496-2511.

Sanghavi, B. J., Varhue, W., Rohani, A., Liao, K. T., Bazydlo, L. A., Chou, C. F. and Swami, N. S., Ultrafast immunoassays by coupling dielectrophoretic biomarker enrichment in nanoslit channel with electrochemical detection on graphene. Lab on a Chip, 2015, 15(24), 4563-4570.

Sharma, H., Digman, M. A., Felsinger, N., Gratton, E., & Khine, M. Enhanced emission of fluorophores on shrink-induced wrinkled composite structures. Optical materials express. 2014, 4(4), 753-763.

Steinberg, W. (1990). The clinical utility of the CA 19-9 tumor-associated antigen. American Journal of Gastroenterology, 85(4).

Tricoli, J. V. and Jacobson, J. W., 2007. MicroRNA: potential for cancer detection, diagnosis, and prognosis. Cancer research, 67(10), pp. 4553-4555.

Varkonyi-Gasic, Erika, et al. "Protocol: a highly sensitive RT-PCR method for detection and quantification of microRNAs." Plant methods 3.1 (2007): 12.

Velmanickam, Logeeshan, et al. "Integrated dielectrophoretic and surface plasmonic platform for million-fold improvement in the detection of fluorescent events." Biomicrofluidics 11.4 (2017): 044115.

Vomhof-DeKrey, E. E., Hermann, R. J., Palmer, M. F., Benton, K. D., Sandy, A. R., Dorsam, S. T. and Dorsam, G. P., 2008. TCR signaling and environment affect vasoactive intestinal peptide receptor-1 (VPAC-1) expression in primary mouse CD4 T cells. Brain, behavior, and immunity, 22(7), pp. 1032-1040.

Wang, X. B., Yang, J., Huang, Y., Vykoukal, J., Becker, F. F. and Gascoyne, P. R., 2000. Cell separation by dielectrophoretic field-flow-fractionation. Analytical Chemistry, 72(4), pp. 832-839.

Wei, Juan, et al. "Identification of plasma microRNA-21 as a biomarker for early detection and chemosensitivity of non-small cell lung cancer." Chinese journal of cancer 30.6 (2011): 407.

Wen, Y., Pei, H., Shen, Y., Xi, J., Lin, M., Lu, N., Shen, X., Li, J. and Fan, C., 2012. DNA nanostructure-based interfacial engineering for PCR-free ultrasensitive electrochemical analysis of microRNA. Scientific reports, 2, p. 867.

White, I. M., Yazdi, S. H. and Wei, W. Y. Optofluidic SERS: synergizing photonics and microfluidics for chemical and biological analysis. *Microfluidics and nanofluidics*. 2012, 13(2), 205-216.

Wolcott, M. J., Advances in nucleic acid-based detection methods. *Clinical microbiology reviews*, 1992, 5(4), 370-386.

Yin, Huanshun, et al. "An electrochemical signal 'off-on' sensing platform for microRNA detection." Analyst 137.6 (2012): 1389-1395.

Zheng, L., Brody, J. P. and Burke, P. J., Electronic manipulation of DNA, proteins, and nanoparticles for potential circuit assembly. *Biosensors and Bioelectronics*, 2004, 20(3), 606-619.

Zou, Z., Kai, J., Rust, M. J., Han, J., & Ahn, C. H. Functionalized nano interdigitated electrodes arrays on polymer with integrated microfluidics for direct bio-affinity sensing using impedimetric measurement. *Sensors and Actuators A: Physical*. 2007, 136(2), 518-526.

It will be understood that various details of the presently disclosed subject matter can be changed without departing from the scope of the subject matter disclosed herein. Furthermore, the foregoing description is for the purpose of illustration only, and not for the purpose of limitation.

The invention claimed is:

1. An interdigitated electrode apparatus to quantify biomarkers in low conductivity buffers, comprising:
   an array of interdigitated T-shaped microelectrodes wherein the distance between the microelectrodes is from about 10 µm to about 100 µm;
   glass substrate;
   conductive metal;
   a well for receiving biological samples;
   wherein the T-shaped microelectrodes comprises rough edges and generates hotspots at the periphery of the T-shaped microelectrodes; and
   wherein the T-shaped microelectrodes are layered between the glass substrate and the conductive metal within the well for receiving biological samples and assembled as a unitary device.

2. The apparatus of claim 1, wherein the conductive metal is Au or Ag.

3. An interdigitated electrode apparatus to quantify biomarkers in low conductivity buffers, comprising:
   an array of interdigitated pearl-shaped microelectrodes wherein the distance between the microelectrodes is from about 10 µm to about 100 µm;
   glass substrate;
   conductive metal;
   a well for receiving biological samples;
   wherein the pearl-shaped microelectrodes comprises rough edges and generates hotspots at the periphery of the pearl-shaped microelectrodes; and
   wherein the pearl-shaped microelectrodes are layered between the glass substrate and the conductive metal within the well for receiving biological samples and assembled as a unitary device.

4. The apparatus of claim 3, wherein the conductive metal is Au or Ag.

* * * * *